(12) United States Patent
Peled et al.

(10) Patent No.: US 7,488,717 B2
(45) Date of Patent: Feb. 10, 2009

(54) METHODS OF INHIBITING CHEMOKINE BINDING TO CHEMOKINE RECEPTORS

(75) Inventors: Amnon Peled, Tel Aviv (IL); Orly Eizenberg, Rehovot (IL); Dalit Vaizel-Ohayon, Nes Ziona (IL)

(73) Assignee: Biokine Therapeutics Ltd., Nes Ziona (IL)

( * ) Notice: Subject to any disclaimer, the term of this patent is extended or adjusted under 35 U.S.C. 154(b) by 362 days.

(21) Appl. No.: 10/649,873

(22) Filed: Aug. 28, 2003

(65) Prior Publication Data

US 2004/0171552 A1    Sep. 2, 2004

Related U.S. Application Data

(63) Continuation-in-part of application No. PCT/IL03/00155, filed on Feb. 27, 2003.

(60) Provisional application No. 60/359,995, filed on Feb. 28, 2002.

(51) Int. Cl.
*A61K 38/00*    (2006.01)
*A61K 39/00*    (2006.01)

(52) U.S. Cl. .......................... 514/14; 514/2; 424/185.1; 530/300

(58) Field of Classification Search .................. None
See application file for complete search history.

(56) References Cited

U.S. PATENT DOCUMENTS

| 5,840,693 A * | 11/1998 | Eriksson et al. ............... 514/12 |
| 2003/0027751 A1* | 2/2003 | Kovesdi et al. ............... 514/12 |
| 2003/0166004 A1* | 9/2003 | Gyuris et al. ............... 435/7.1 |
| 2004/0171552 A1 | 9/2004 | Peled et al. |

FOREIGN PATENT DOCUMENTS

| WO | WO 02/061087 | 8/2002 |
| WO | WO 03/072599 | 4/2003 |

OTHER PUBLICATIONS

Hay DWP et al. Interleukin-8 receptor antagonists in pulmonary diseases. Current Opinion in Pharmacology. 2001. vol. 1, pp. 242-247.*

Mukaida N. et al. Interleukin-8 and other CXC chemokines. In The Cytokine Handbook. vol. 2, 4th Ed. Thomson and Lotze Eds. Academic Press, 2003.*

Burmer et al. "G Protein-Coupled Receptor (GPCR) Antigenic Peptide Seq Id No. 944", Retrieved From EBI Database Accession No. ABP82271, 2003. Abstract.

Proudfoot et al. "The Strategy of Blocking the Chemokine System to Combat Disease", Immunological Reviews, 177: 247-256, 2000. p. 253-255.

Hayashi et al. "Synthetic Hexa- and Heptapeptides That Inhibit IL-8 From Binding to and Activating Human Blood Neutrophils 1", The Journal of Immunology, 154: 814-824, 1995.

Misumi et al. "A Cyclic Dodecapeptide-Multiple-Antigen Peptide Conjugate From the Undecapeptidyl Arch (From Arg168 to Cys178) of Extracellular Loop 2 in CCR5 as A Novel Human Immunodeficiency Virus Type 1 Vaccine", Journal of Virology, 75(23): 11614-11620, 2001.

Misumi et al. "A Novel Cyclic Peptide Immunization Strategy for Preventing HIV-1/AIDS Infection and Progression", The American Society for Biochemistry and Molecular Biology, p. 1-38, 2003.

Baggiolini et al. "CC Chemokines in Allergic Inflammation", Immunology Today, 15(3): 127-133, 1994.

Cocchi et al. "Identification of RANTES, MIP-1α, and MIP-1β as the Major HIV-Suppressive Factors Produced by CD8= T Cells", Science, 270: 1811-1815, 1995.

Ma et al. "Impaired B-Lymphopoiesis, Myelopoiesis, and Derailed Cerebellar Neuron Migration in CXCR4- and SDF-1-Deficient Mice", Proc. Natl. Acad. Sci. USA, 95: 9448-9453, 1998.

Müller et al. "Involvement of Chemokine Receptors in Breast Cancer Metastasis", Nature, 410: 50-56, 2001.

Strieter et al. "The Functional Role of the ELR Motif in CXC Chemokine-Mediated Angiogenesis", The Journal of Biological Chemistry, 270(45): 27348-27357, 1995.

Vaddi et al. "Regulation of Monocyte Integrin Expression by β-Family Chemokines", The Journal of Immunology, 153: 4721-4732, 1994.

* cited by examiner

*Primary Examiner*—Robert Landsman
*Assistant Examiner*—Bruce D. Hissong

(57) ABSTRACT

Novel peptides or peptidomimetic agents or small molecules for modulating the biological effect of a chemokine. According to the present invention, the therapeutic agents preferably are endowed with the capacity to bind to certain chemokines in order to modulate the biological interaction between the target ligand, chemokine, and the respective target receptor, chemokine receptor. These peptides may be described as agonist ligands or antagonists. Next, preferably certain peptides share consensus sequences are described which characterize the families or categories of these modulator peptides.

4 Claims, 5 Drawing Sheets

Fig. 4a
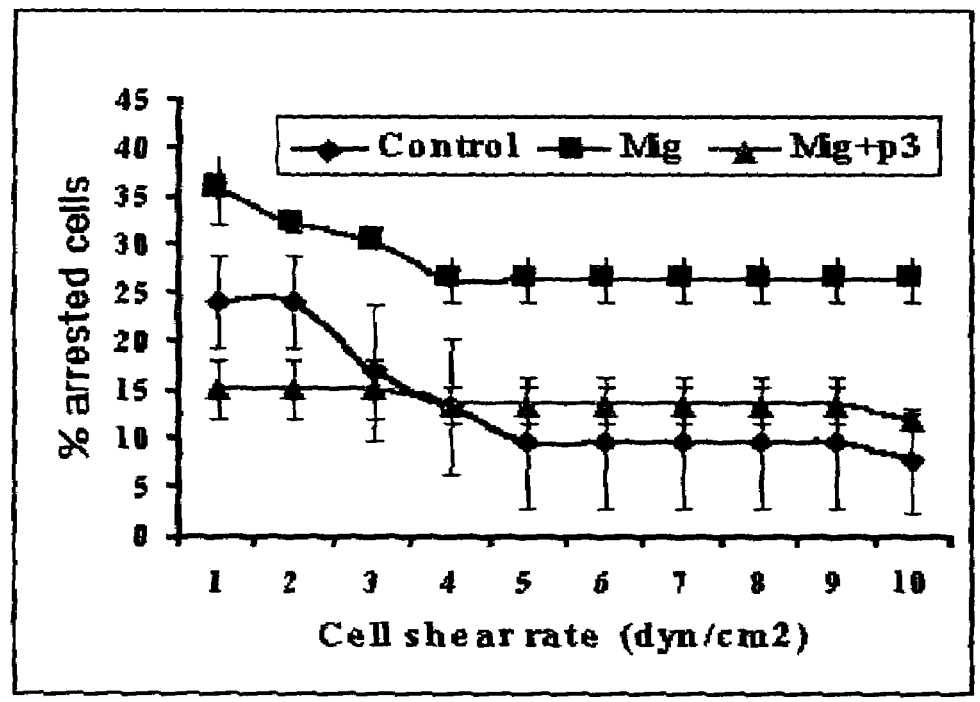
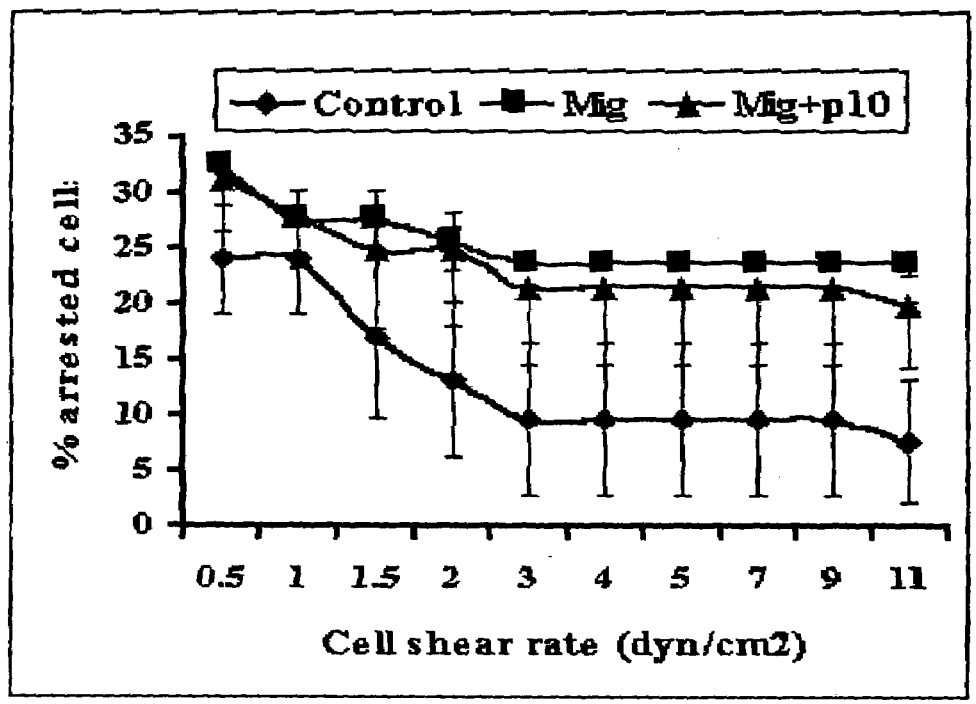
Fig. 4b

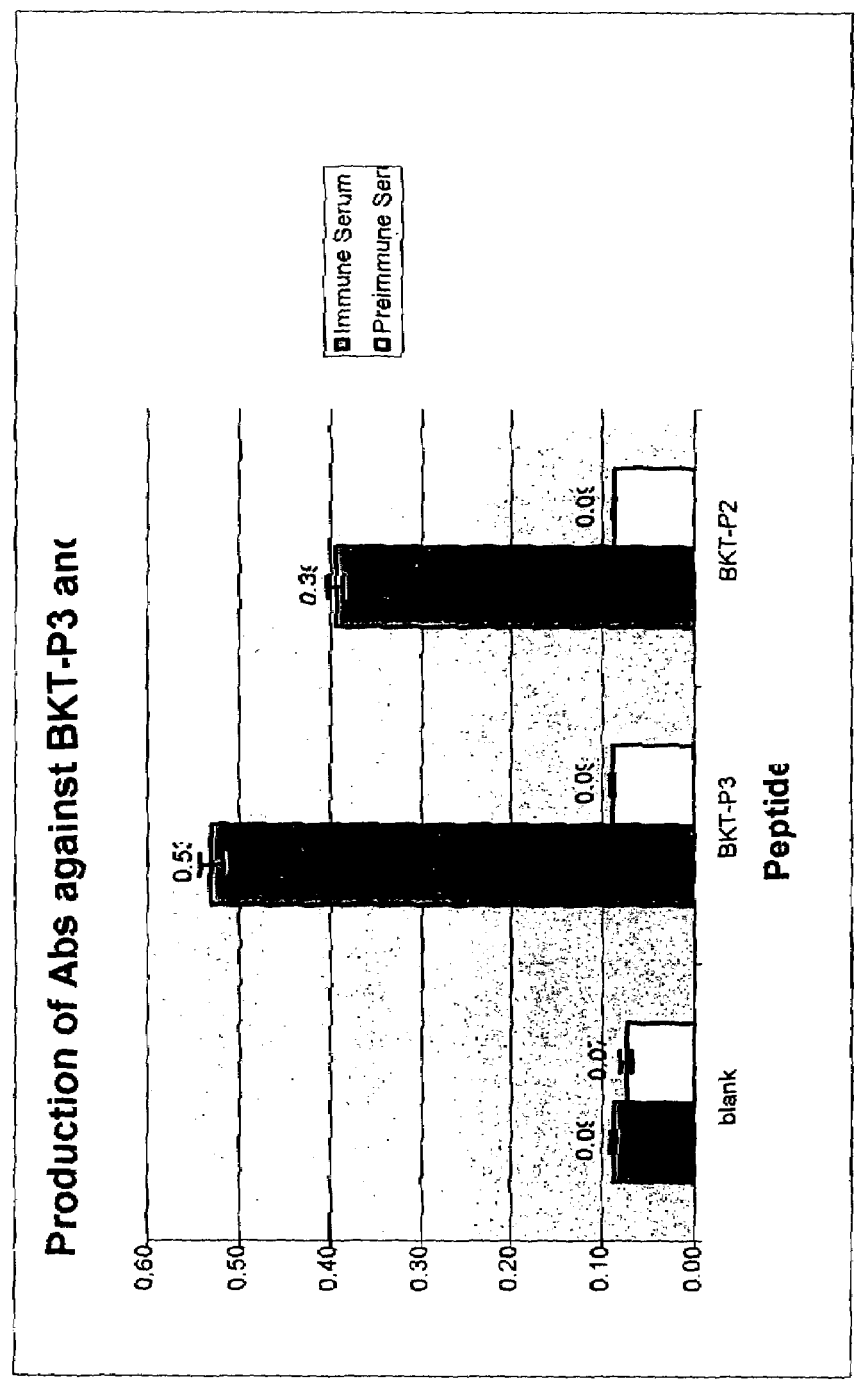

METHODS OF INHIBITING CHEMOKINE BINDING TO CHEMOKINE RECEPTORS

This Application is a Continuation-in-Part of PCT Application No. PCT/IL03/00155, filed 27 Feb. 2003, currently pending, which claims priority from 60/359,995, filed 28 Feb. 2002, now expired, all of which are hereby incorporated by reference as if fully set forth herein.

FIELD OF THE INVENTION

The present invention discloses novel peptidic molecules or peptidomimetic agents, which are capable of binding chemokines and modulating their biological functions.

BACKGROUND OF THE INVENTION

Drug discovery in the post-genomics era provides enormous opportunities as well as new challenges. The targets of the drug discovery process have changed greatly over the last 50 years. The development of advanced purification technologies and the tools of molecular biology have brought molecular targets into the current discovery process. In the last ten years, there has been a trend towards selecting molecular targets for the screening process, and the human and other genome projects have made available many thousands of additional targets for drug discovery.

In addition to these novel targets with unknown potential, there are a significant number of well-validated targets associated with major human diseases. Most of these are either nuclear receptors or G protein-coupled receptors. It was found, that in some cases, one compound that has an effect through one receptor, can also act through another receptor, and that several compounds can work through the same receptor. Unfortunately, even when the mechanism of a disease process is understood, for example by identifying the receptor(s) responsible for such a process, this information has not always resulted in the development of new treatments. For example, subjects who suffer from inflammation associated diseases and disorders have a great and desperate demand for novel drugs as therapeutic agents. Current therapies are merely palliative and have not been significantly improved in recent years.

Recent scientific advances provide some hope that new treatments will soon be available for these diseases. Sequencing of the human genome, which contains nearly 30,000 genes, has been recently completed. This significant achievement in the frontiers of human medicine will allow the identification of genes involved in the onset and progression of human diseases and pathological states. Many of these genes will serve as valid targets in the discovery process of drugs that are more effective in the treatment of inflammatory diseases. Along with a massive flow of novel genes with potential therapeutic properties, there is a growing need for more rapid and efficient ways to discover lead compounds with enhanced (agonistic) or inhibitory (antagonistic) properties.

Chemokines are among the biological factors that are, amongst other functions, involved in the inflammatory disease process. Chemokines belong to a group of small, ~8-14 kDa, mostly basic, heparin binding proteins that are related both in their primary structure and the presence of 4 conserved cysteine residues. The chemokines are chemotactic cytokines that have been shown to be selective chemoattractants for leukocyte sub-populations in vitro, and to elicit the accumulation of inflammatory cells in vivo. In addition to chemotaxis, chemokines mediate leukocyte de-granulation (Baggiolini and Dahinden, 1994) and the up-regulation of adhesion receptors (Vaddi and Newton, 1994), and have recently been implicated in the suppression of human immunodeficiency virus replication (Cocchi et al., 1995).

Chemokines can be divided into 4 groups (CXC, CX3C, CC, and C) according to the positioning of the first 2 closely paired and highly conserved cysteines of the amino acid sequence. The specific effects of chemokines on their target cells, are mediated by members of a family of 7-transmembrane-spanning G-protein-coupled receptors. These chemokine receptors are part of a much bigger super family of G-protein-coupled receptors that include receptors for hormones, neurotransmitters, paracrine substances, inflammatory mediators, certain proteinases, taste and odorant molecules and even photons and calcium ions.

The chemokine receptors have received increasing attention due to their critical role in the progression of immune disease states such as asthma, atherosclerosis, graft rejection, AIDS, multiple sclerosis and others. It would be useful to have therapeutic agents capable of inhibiting the binding of ligands of some chemokine receptors in order to lessen the intensity of or cure these diseases. Chemokines themselves play an essential role in the recruitment and activation of cells from the immune system. They also have a wide range of effects in many different cell types beyond the immune system, including for example, in various cells of the central nervous system (Ma et al., 1998) or endothelial cells, where they result in either angiogenic or angiostatic effects (Strieter et al., 1995). Recent work has shown that particular chemokines may have multiple effects on tumors, including promoting growth, angiogenesis, metastasis, and suppression of the immune response to cancer, while other chemokines inhibit tumor mediated angiogenesis and promote anti-tumor immune responses.

Recently, it was shown that the SDF-1α/CXCR4 chemokine/chemokine receptor pathway is involved in dissemination of metastatic breast carcinomas (Muller A, 2001). This example illustrates that both chemokines and their receptors are potentially valuable targets for therapeutic intervention in a wide range of diseases.

SUMMARY OF THE INVENTION

The background art does not teach or suggest sequences or compositions containing peptidic modulators capable of binding to chemokines and inhibiting or activating their biological functions. The background art also does not teach or suggest sequences or compositions containing the basic consensus sequences that characterize families of such peptidic chemokine-binding modulators. In addition, the background art does not teach or suggest the nucleic acid molecules encoding for such peptidic chemokine-binding modulators. Finally, the background art does not teach or suggest methods of treatment employing such peptidic chemokine-binding modulators.

The present invention overcomes these deficiencies of the background art by providing peptidic chemokine-binding modulators, with defined amino acid sequences, which have been found to bind to specific chemokines, including but not limited to human SDF-1α, MIG, IL-8, MCP-1 and Eotaxin, and which modulate the binding of these chemokines to their respective receptors and/or which otherwise have an inhibitory or stimulatory effect on the biological activity of chemokines.

It should be noted that the term "peptidic" as used herein, also includes peptidomimetics and hybrid structures comprised of at least one amino acid and at least one molecule that is not an amino acid, or at least not a naturally occurring amino acid. The term amino acid may optionally also include non-naturally occurring amino acids as well as naturally occurring amino acids, and derivatives and analogs thereof.

A peptide mimetic (peptidomimetic) is a molecule that mimics the biological activity of a peptide, yet is no longer peptidic in chemical nature. By strict definition, a peptidomimetic is a molecule that no longer contains any peptide bonds, i.e., amide bonds between amino acids; however, in the context of the present invention, the term peptide mimetic and also the term peptidomimetic are intended to include molecules that are no longer completely peptidic in nature, such as pseudo-peptides, semi-peptides and peptoids. Whether completely or partially nonpeptide, peptidomimetics according to the present invention provide a spatial arrangement of reactive chemical moieties that closely resembles the three-dimensional arrangement of active groups in the peptide on which the peptidomimetic is based. The techniques of developing peptidomimetics are conventional. Thus, non-peptide bonds that allow the peptidomimetic to adopt a similar structure to the original peptide can replace peptide bonds.

Replacing chemical groups of the amino acids with other chemical groups of similar structure can also be used to develop peptidomimetics.

Preferably, the present invention features basic consensus sequences, some of which characterize families of such peptidic chemokine-binding modulators.

More specifically, if the biological activity caused by the target protein, i.e. chemokine receptor, when activated through binding the target ligand, i.e. chemokine, involves activation of some biological function, then the inhibitory peptide preferably inhibits such activation. On the other hand, if the biological activity caused by the receptor involves inhibition of some biological function, then the inhibitory peptide preferably blocks inhibition of the biological function.

According to another preferred embodiment of the present invention, there is provided a composition for treating inflammatory and cancer metastasis conditions in a subject, comprising a pharmaceutically effective amount of a therapeutic agent for administering to the subject, the therapeutic agent being composed of the peptidic chemokine-binding modulators as the active ingredient as well as a suitable pharmaceutical carrier if necessary.

According to a preferred embodiment of the present invention, the therapeutic agent may be administered topically, intranasally and by inhalation. Alternately, the therapeutic agent may be administered by systemic administration.

According to the present invention, there is provided a peptidic chemokine modulator for modulating a biological effect of a chemokine, comprising a molecule having a defined amino acid composition.

According to another embodiment of the present invention, there is provided a peptidic chemokine modulator for modulating a biological effect of a chemokine, comprising a molecule composed of the amino acids H, S, A, L, I, K, R, T and P, and featuring at least 2 Histidines spread along the molecule, wherein the molecule features an overall positive charge (family 1). The present invention comprises peptides having these characteristics and preferably being up to about 20 amino acids in length, more preferably from about 10 to about 20 amino acids in length, and optionally and most preferably about 12 amino acids in length. Preferably, the molecule comprises a peptide having an amino acid sequence selected from the group consisting of SIFAHQTPTHKN (seq id no:100), SIPSHSIHSAKA (seq id no:101), SAISDHRAHRSH (seq id no:96), SAGHIHEAHRPL (seq id no:95), ACHASLKHRC (seq id no. 44), AHSLKSITNHGL (seq id no:46), ESDLTHALHWLG (seq id no:54), HSA-CHASLKHRC (seq id no:69), WSAHIVPYSHKP (seq id no:143), YATQHNWRLKHE (seq id no:145), CAHLSPHKC (seq id no:1), GVHKHFYSRWLG (seq id no:61), HPTTPFIHMPNF (seq id no:66), SVQTRPLFHSHF (seq id no:113), and VHTSLLQKBPLP (seq id no:133). More preferably, the peptide has an amino acid sequence SIFAHQTPTHKN (seq id no:100). The peptidic chemokine modulator may optionally be used for binding to a chemokine selected from the group comprising MIG, MCP-1, IL-8, SDF-1 alpha and Eotaxin.

According to another embodiment of the present invention, there is provided a peptidic chemokine modulator for modulating a biological effect of a chemokine, comprising a molecule composed of the amino acids H, P, T, L, R, W, F, and featuring at least two neighboring histidines, wherein the molecule features an overall positive charge (family 2). The present invention comprises peptides having these characteristics and preferably being up to about 20 amino acids in length, more preferably from about 10 to about 20 amino acids in length, and optionally and most preferably about 12 amino acids in length. Preferably, the molecule comprises a peptide having an amino acid sequence selected from the group consisting of GDFNSGHHTTTR (seq id no:59), HHFHLPKLRPPV (seq id no:64), HHTWDTRIWQAF (seq id no:65), LDYPIPQTVLHH (seq id no:76), LLADTTHHRPWP (seq id no:79), TRLVPSRYYHHP (seq id no:125), CHHNLSWEC (seq id no:7) and SFWHHHSPRSPL (seq id no:99). More preferably, the peptide has an amino acid sequence LLADTTHHRPWP (seq id no 79:).

According to another embodiment of the present invention, there is provided at least one peptide having at least 90% sequence homology, more preferably about 95% sequence homology, and most preferably sequence identity to any peptide listed in any of the Tables herein and/or in the specification, that is preferably up to about 20 amino acids in length, more preferably from about 10 to about 20 amino acids in length, and optionally and most preferably about 12 amino acids in length. A peptide according to the present invention may optionally belong to one of the two families, or may alternatively not belong to either family.

Hereinafter, homology is defined as that which is determined with the Smith-Waterman algorithm, using the Bioaccelerator platform developed by Compugene (gapop: 10.0, gapext: 0.5, matrix: blosum62).

According to another embodiment of the present invention, there is provided a composition for treating a condition involving abnormal cell migration in a subject, the composition comprising a pharmaceutically effective amount of a therapeutic agent for administering to the subject, the therapeutic agent comprising a chemokine modulator as described above. Preferably, the condition comprises an inflammatory condition. Alternatively, the condition comprises cancer metastasis. Optionally, the therapeutic agent is administered by topical administration, such that the composition further comprises a pharmaceutically acceptable carrier for topical administration. Preferably, the topical administration is to the skin of the subject. Optionally, the therapeutic agent is administered by inhalation, such that the composition further comprises a pharmaceutically acceptable carrier for inhalation. Alternatively, the therapeutic agent is administered intranasally, such that the composition further comprises a pharmaceutically acceptable carrier for intranasal administration.

Optionally, the therapeutic agent is characterized by an ability to inhibit binding of the chemokine to a chemokine receptor.

Optionally, the therapeutic agent is characterized by an ability to enhance binding of the chemokine to a chemokine receptor.

According to another embodiment of the present invention, there is provided a method for treating a disease modulated through and/or caused by binding of a chemokine to a chemokine receptor in a subject, comprising administering a pharmaceutically effective amount of a therapeutic agent to the subject, the therapeutic agent comprising a peptidic chemokine modulator as described above.

Preferably, the therapeutic agent binds to at least one of the chemokines and wherein the therapeutic agent directly modulates the activity of the chemokine by modulation of binding to the chemokine receptor.

Optionally and preferably, the disease is selected from the group consisting of: inflammation (primary or secondary), allergy, a non-optimal immune response, an autoimmune reaction (including rheumatoid arthritis, systemic lupus erythematosis, multiple sclerosis and others), allograft rejection, diabetes, sepsis, cancer and any type of malignant cell growth, acute and chronic bacterial and viral infections, arthritis, colitis, psoriasis, atherosclerosis, hypertension and reperfusion ischemia.

According to still another embodiment of the present invention, there is provided an antibody for binding to a chemokine-binding receptor, comprising: an antibody being capable of recognizing at least a portion of a chemokine-binding receptor, wherein the antibody also recognizes a peptide having a sequence as described above.

Optionally, there is also provided a vaccine formed with the above antibody.

According to still another embodiment of the present invention, there is provided a method for producing an antibody, comprising: inducing formation of antibody against a peptide having a sequence according to the above description, wherein the antibody is also capable of recognizing a chemokine-binding receptor.

Preferably, the antibody comprises a monoclonal antibody. Alternatively, the antibody comprises a polyclonal antibody. Preferably, the antibody forms a vaccine.

The peptidic chemokine-binding modulators are then preferably used to develop one or more lead compounds for new therapies. Alternatively or additionally, the peptidic chemokine-binding modulators themselves may have therapeutic value, and as such, may optionally be used for treatment of a subject.

Also additionally or alternatively, binding of the peptidic chemokine-binding modulators may optionally be used to identify lead proteins, which are reference proteins whose reactivity descriptors are substantially similar to those of the protein of interest such as novel chemokine binding proteins. By "reactivity descriptor" it is meant the characteristics of binding to other chemokines and/or chemokine binding proteins, and/or the biological activity induced and/or inhibited by the reference protein.

Also additionally or alternatively, the peptidic chemokine-binding modulators may optionally be used as antigens to produce antibodies to these peptides, which can also bind chemokine-binding receptors, or optionally may be used to stimulate the production of auto-antibodies against these peptides that can also bind chemokine receptors. The latter use would involve using these peptides (or other modulators) as a vaccine, optionally with any suitable vaccine carrier that could easily be selected by one of ordinary skill in the art, including but not limited to, adjuvants, carriers and the like. More preferably, the modulators that are used to produce the antibodies are selected from one of the peptides described herein. It should be noted that the vaccine may also optionally comprise the antibody itself.

Hereinafter, the term "biologically active" refers to molecules, or complexes thereof, which are capable of exerting an effect in a biological system. Hereinafter, the term "fragment" refers to a portion of a molecule or a complex thereof, in which the portion includes substantially less than the entirety of the molecule or the complex thereof.

Hereinafter, the term "amino acid" refers to both natural and synthetic molecules that are capable of forming a peptide bond with another such molecule. Hereinafter, the term "natural amino acid" refers to all naturally occurring amino acids, including both regular and non-regular natural amino acids. Hereinafter, the term "regular natural amino acid" refers to those alpha amino acids that are normally used as components of a protein. Hereinafter, the term "non-regular natural amino acid" refers to naturally occurring amino acids, produced by mammalian or non-mammalian eukaryotes, or by prokaryotes, which are not usually used as a component of a protein by eukaryotes or prokaryotes. Hereinafter, the term "synthetic amino acid" refers to all molecules which are artificially produced and which do not occur naturally in eukaryotes or prokaryotes, but which fulfill the required characteristics of an amino acid as defined above. Hereinafter, the term "peptide" includes both a chain and a sequence of amino acids, whether natural, synthetic or recombinant. Hereinafter, the term "peptidomimetic" includes both peptide analogues and mimetics having substantially similar or identical functionality thereof, including analogues having synthetic and natural amino acids, wherein the peptide bonds may be replaced by other covalent linkages.

BRIEF DESCRIPTION OF THE DRAWINGS AND TABLES

The invention is herein described, by way of example only, with reference to the accompanying drawings and tables, wherein:

FIG. 1 shows the results of binding of chemokines to BKT-P1, BKT-P3, BKT-P22, and BKT-P37 peptides, which bind, respectively, to at least one of the following chemokines, SDF-1α, MCP-1, Eotaxin and IL-8;

FIG. 2 shows the binding of synthetic peptides from Table 1 which can either bind specifically to various chemokines (such as BKT-P 1, shown in FIG. 2B), or can alternatively bind specifically to a single chemokine (such as BKT-P9 alone, as shown in FIG. 2A);

FIG. 3 shows the results of binding of one of the synthetic peptides from family 1, BKT P3, to various chemokines. BKT-P18, which does not belong to the family, is shown as a control;

FIG. 4 shows a graphical representation of the biological activity results for BKT-P3, from family 1 in a biovalidation assay system in which the chemokine MIG and the adhesion receptor VCAM-1 are used to activate the binding of T cells (see "Material and Methods") (FIG. 4A); BKT-P10, which does not belong to the family, is shown as a control (FIG. 4B).

FIG. 5 shows a graphical representation of the level of immnunity (O.D.) of antibody raised against BKT-P3 and BKT-P2, both of which belong to family 1, to the relevant peptides, BKT-P3 and BKT-P2. The preimmune serum of the same mice used as a control. "Blank" is the O.D. level of antibody binding to the plastic (of the Elisa experiment), with no addition of peptides.

Table 1 shows the sequences of peptides that bind to the chemokines MCP-1, SDF-1α, MIG, Eotaxin and IL-8;

Table 2 shows a family of peptides (family no. 1) that bind to MIG, MCP-1, IL-8, SDF-1α and Eotaxin and are predominantly composed of the amino acids H, S, A, L, I, K, R, T and P, featuring at least 2 Histidines spread along the molecule. The abundance of positively charged amino acids such as H, K and R, resulted in peptides having an overall positive charge. The remaining amino acids, mentioned above, might participate in the determination of the three dimensional structure of the peptides;

Table 3 shows a family of peptides (family no. 2) that bind mostly to MCP-1 and in individual cases to IL-8, SDF-1α and Eotaxin; the binding motif for peptides in this family is predominantly composed of the amino acids H, P, T, L, R, W, F, featuring at least 2 Histidines next to each other. The abundance of positively charged amino acids, such as H and R, resulted in peptides having an overall positive charge. The remaining amino acids, mentioned above, might participate in the determination of the three dimensional structure of the peptides;

Table 4 shows a summary of the results of the biological activity of four representatives from family 1, in a biovalidation assay system, in which various chemokines and the adhesion receptor VCAM-1 are used to activate the binding of T cells (as described in "Materials and Methods").

Table 5 shows a summary of the results of the biological activity of two representatives from Table 1, which do not belong to either family 1 or family 2, in a biovalidation assay system, in which various chemokines and the adhesion receptor VCAM-1 are used to activate the binding of T cells (as described in "Materials and Methods").

Table 6 shows the list of synthetic peptides that were ordered for further analysis of their ability to modulate chemokine activity.

DESCRIPTION OF THE PREFERRED EMBODIMENTS

The present invention is composed of peptidic modulatory molecules with defined amino acid sequences which have been found to bind to specific chemokines, including, but not limited to, human SDF-1α, MIG, IL-8, MCP-1 and Eotaxin, and which inhibit or stimulate the binding of these chemokines to their respective receptor/s and/or which otherwise have an inhibitory or stimulatory effect on the biological activity of chemokines. Preferably, the present invention specifies basic consensus sequences, with overall positive electrostatic charge, which characterize families of such modulatory chemokine-binding peptide molecule.

The chemokine binding peptides mimic chemokine receptor structures or motifs. It is therefore predicted that the alpha-chemokine-binding peptides, when injected or otherwise introduced into mice or humans, may produce antibodies against chemokine receptors that can be either used for the production of monoclonal antibodies or used for development of a vaccine against a particular chemokine receptor/s. Whether antibodies are produced, or alternatively, binding to a particular chemokine receptor is blocked and/or enhanced, may depend upon the method of introduction to the subject. For example, antibody production may be potentiated if the peptides (and/or other peptidic modulatory molecule according to the present invention) are introduced with an adjuvant. Concentration of the peptide or other molecule may also be important. In any case, one of ordinary skill in the art could easily determine conditions for antibody production, as opposed to having the effect potentiated or mediated directly through the peptides and/or other peptidic modulatory molecules according to the present invention.

The modulatory chemokine-binding peptide molecules of the present invention could therefore be useful for treating a disease selected from the group consisting of inflammation (primary or secondary e.g. uveitis, bowel inflammation), allergy, non-optimal immune response, autoimmune reaction (including rheumatoid arthritis, systemic lupus erythematosis, multiple sclerosis and others), delayed-type hypersensitivity, allograft rejection, diabetes, sepsis, cancer and any type of malignant cell growth, (including, but not limited to breast cancers such as infiltrating duct carcinoma of the breast or other metastatic breast cancers, lung cancers such as small cell lung carcinoma, bone cancers, bladder cancers such as bladder carcinoma, rhabdomyosarcoma, angiosarcoma, adenocarcinoma of the colon, prostate or pancreas, or other metastatic prostate or colon cancers, squamous cell carcinoma of the cervix, ovarian cancer, malignant fibrous histiocytoma, skin cancers such as malignant melanoma, lymphomas and leukemia, leiomyosarcoma, astrocytoma, glioma and heptocellular carcinoma), acute and chronic bacterial and viral infections, vasculitis, arthritis, colitis, psoriasis, atherosclerosis, Graves disease, anorexia nervosa; hemorrhagic shock caused by septicemia, HIV infection in AIDS, pemphigus, asthma, renal diseases, liver diseases, bone marrow failure, vitiligo, alopecia, and myositis, hypertension and reperfusion ischemia.

The examples provided below, describe certain experiments performed with the peptidic modulatory of the present invention, demonstrating the binding efficacy of these molecules to the various chemokines. It also demonstrates the efficacy of the peptidic chemokine-binding modulator in a biological system. In addition, the examples also describe formulations for administering the compounds of the present invention, and methods of treatment thereof.

EXAMPLE 1

Efficacy of the Peptides of the Present Invention

This Example demonstrates the efficacy of the peptidic chemokine-binding modulators of the present invention, in a number of different assays, including binding assays and assays for measuring a functional biological effect.

Materials and Methods

Chemokines

Recombinant chemokines were ordered from PeproTech, Inc. (Rocky Hill, N.J. USA). Human SDF-1α (Cat. No. 300-28A), human MIG (Cat. No. 300-26) and human IL-8, (72 amino acids) (Cat. No. 200-08M), belong to the alpha-chemokines (C-X-C) family. Human MCP-1 (MCAF) (Cat. No. 300-04) and human Eotaxin (Cat No. 300-21) belong to the beta-chemokines (C-C family). All chemokines were prepared according to the company recommendations.

Peptide Synthesis

Peptides were synthesized in the Weizmann Institute of Science, Rehovot, Israel, in order to perform tests for characterization of their influence on the biological activity of the chemokines. The format of the various synthesized peptides was as follows: The cyclic peptides, $ACX_7CGGGSK$-biotin-G and the linear peptides, $X_{12}GGGSK$-biotin-G. The peptides were biotinylated on their C-termini; the biotin will serve as a detector during the following experiments. Each synthetic peptide was dissolved to concentration of 1 mg/ml (~0.6 mM) in 4% DMSO (Dimethyl Sulphoxide, Sigma, Cat. # D-2650).

ELISA Analysis of the Synthetic Chemokine-binding Peptide

NUNC-Immuno maxisorp plates (Cat. No. 4-42404) were coated with the appropriate chemokine (0.1 ml/well, 0.1-1.0 µg/ml in 0.1 M NaHCO$_3$, pH 8.6), overnight at 4° C. The plates were then blocked with 0.2 ml/well of blocking buffer (5 mg/ml BSA in 0.1 NaHCO$_3$). Control wells were treated with blocking buffer alone, with no addition of target protein (chemokine). The plates were washed 6 times with PBST (0.1% TWEEN® 20 (polyoxyethylene (20) sorbitan monolaurate) in PBS), followed by incubation for 45 minutes at room temperature with 10-fold serial dilutions of individual synthetic peptides (10 pg-10 µg) with 1%BSA (PBST-BSA)/ well. After the plates were washed 6 times with PBST, the bound peptides were probed by HRP-SA Conjugate, diluted 1:10,000 to 1:20,000 in PBST-BSA, 0.1 ml/well for 45 minutes at room temperature. The target-bound synthetic peptides probed with HRP-SA were quantified by DAKO TMB one-step substrate system, followed by the addition of stop solution, HCl—H$_2$SO$_4$ mixture (0.1 ml/well) (1N HCl, 3N H$_2$SO$_4$). The results were analyzed by ELISA reader at OD$_{450}$.

T-Cell Purification from Fresh Blood 50 ml blood was added to 10 ml Dextran (Dextran T-500 6% w/v) in PBS (phosphate buffer saline), and 7 ml citrate buffer (25 g citrate, 8 g citric acid in 500 ml PBS). The solution was incubated for 30 min at 25° C. 10 ml Ficoll 1077 (Sigma) was added to the bottom of the tube. The tube was then centrifuged at 2,000 rpm for 30 min, at 18° C., (with the brake mode of the centrifuge off). The interphase was collected and washed twice with 8 ml PBS-50% FCS (fetal calf serum), followed by centrifugation at 1,400 rpm, for 5 min, at 18° C. The cells were re-suspended in PBS-5% FCS at a concentration less then 10$^8$/ml. 2 ml of the cell solution were applied and incubated for 45 min at 25° C. on a Perspex Nylon wool column, which was pre-soaked with PBS-5% FCS. Each column was washed with 8 ml PBS-5% FCS and the cells (T-cells and erythrocytes) were eluted by 50 ml of 5 mM EDTA in PBS. A red pellet was obtained by centrifugation at 1,400 rpm, at 4° C., for 5 min, with the brake on. In order to perform lysis of the erythrocytes, the red pellet was re-suspended in 5 ml lysis-buffer (155 mM NH$_4$Cl, 10 mM KHCO$_3$, 0.1 mM EDTA, X0.1PBS) for 4 min, followed by immediate addition of 50 ml of PBS-EDTA.

Following centrifugation at 1,400 rpm, at 4° C., for 5min with brake on, the pellet was washed again with 50 ml PBS-EDTA and re-centrifuged under the same conditions. A white pellet was obtained and re-suspended in RPMI/10% FCS/L-glutamine/sodium pyruvate/antibiotics at a concentration of 3$^x$10$^6$ cells/ml. The cells were incubated for 2 h at 37° C., followed by collection of the non-adherent cells. The cells were ready for use in experiments after overnight incubation at 37° C.

Preparation of Adhesive Substrates

Human VCAM-1 (1 µg/ml) and SDF-1α (intact or heat-inactivated) (2 µg/ml) were dissolved in PBS buffered with 20 mM bicarbonate, pH 8.5, and incubated on a polystyrene plates overnight at 4° C. The plates were then washed three times and blocked with human serum albumin (20 mg/ml in PBS) for 2 h at 37° C.

Biovalidation

Laminar flow assays were performed as follows. Polystyrene plates (B.D) were coated with soluble VCAM-1 at 10 µg/ml in the presence of 2 µg/ml HSA carrier. The plates were washed three times with PBS and blocked with HSA (20 µg/ml in PBS) for 2 hrs at room temperature. Alternatively, washed plates were coated with 10 µg/ml MIG chemokine in PBS for 30 min at room temperature, before being blocked with HSA. The plates were assembled as the lower wall of a parallel wall flow chamber and mounted on the stage of an inverted microscope. The peptide, as described previously, (10 µg/ml) was allowed to settle on the substrate coated chamber wall for 10 min, at 37° C. and then washed. T cells (5×10$^6$/ml, purity >98%) were suspended in binding buffer, perfused into the chamber and allowed to settle on the substrate coated chamber wall for 1 min, at 37° C. Flow was initiated and increased in 2 to 2.5 fold increments every 5 sec. generating controlled shear stresses on the wall. Cells were visualized in a 20x objective of Nikon DIAPHOT TMD Biological Inverted Microscope (Nikon, Japan) and photographed with a long integration LIS-700 CCD video camera (Applitech; Holon, Israel), connected to a video recorder (AG-6730 S-VHS, Panasonic, Japan). The number of adherent cells resisting detachment by the elevated shear forces was determined after each interval by analysis of videotaped cell images, and was expressed as the percent of originally settled cells. All adhesion experiments were performed at least three times on multiple test fields.

Results

Identification of Chemokine Binding Peptides with Antagonistic Effect

The present invention identifies chemokine-binding peptides with biological activity. The binding specificities of the various peptides to the chemokines were determined by screening against BSA, Actin and Fibronectin-coated wells as negative controls in parallel experiments. The binding level of the peptides to the various chemokines, which reached at least two fold of the binding level to the control proteins, was considered a specific binding. The different peptides that were found to bind to chemokines, are listed in Table 1.

Figure 1:
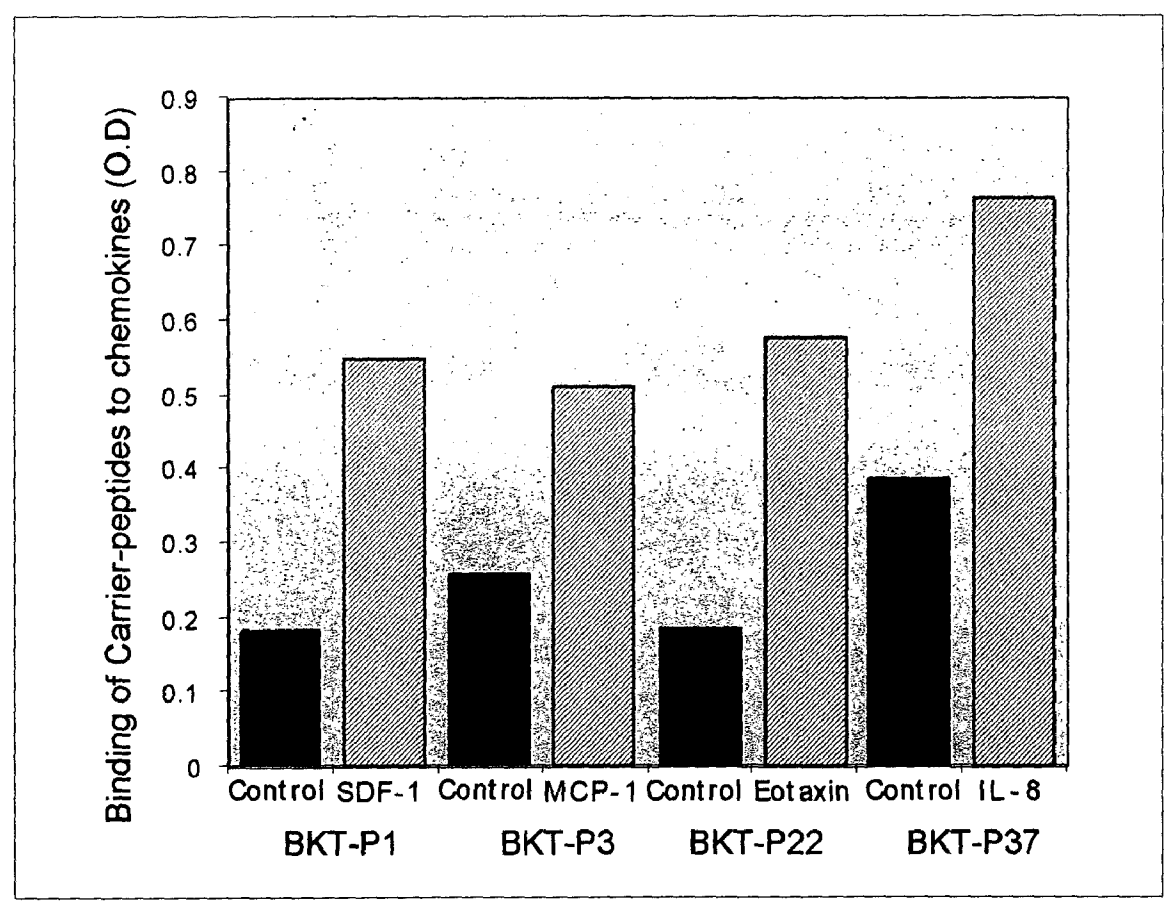

Graphical representations of four examples of such peptide-containing carriers, from the list in Table 1, are shown in FIG. 1. As can be seen, each of those peptides was found to bind to at least one different chemokine, which was chosen to be presented in this graph: peptide BKT-P1 was found to bind SDF-1α; peptide BKT-P3 was found to bind, in this representation, to MCP-1; peptide BKT-P22, was found to bind Eotaxin and peptide BKT-P37, was found to bind IL-8. The specificity of the binding was calculated by comparing the binding level of the proteins to chemokines to that of binding level to control proteins, as explained above. It should also be noted that the binding of each of the peptides shown in FIG. 1 is not necessarily the only binding capability shown by those peptides.

Peptides that showed affinity/binding to one or more chemokines were then analyzed in several individual experiments, and were chosen for further analysis. The specific binding of the peptides was detected by screening methodology, using ELISA, as described in "Materials and Methods", employing microplates coated with the various chemokines to be checked. The binding specificities of the various peptides to the various chemokines were determined by screening against BSA, Actin and Fibronectin-coated wells as negative controls in parallel experiments.

Figure 2:
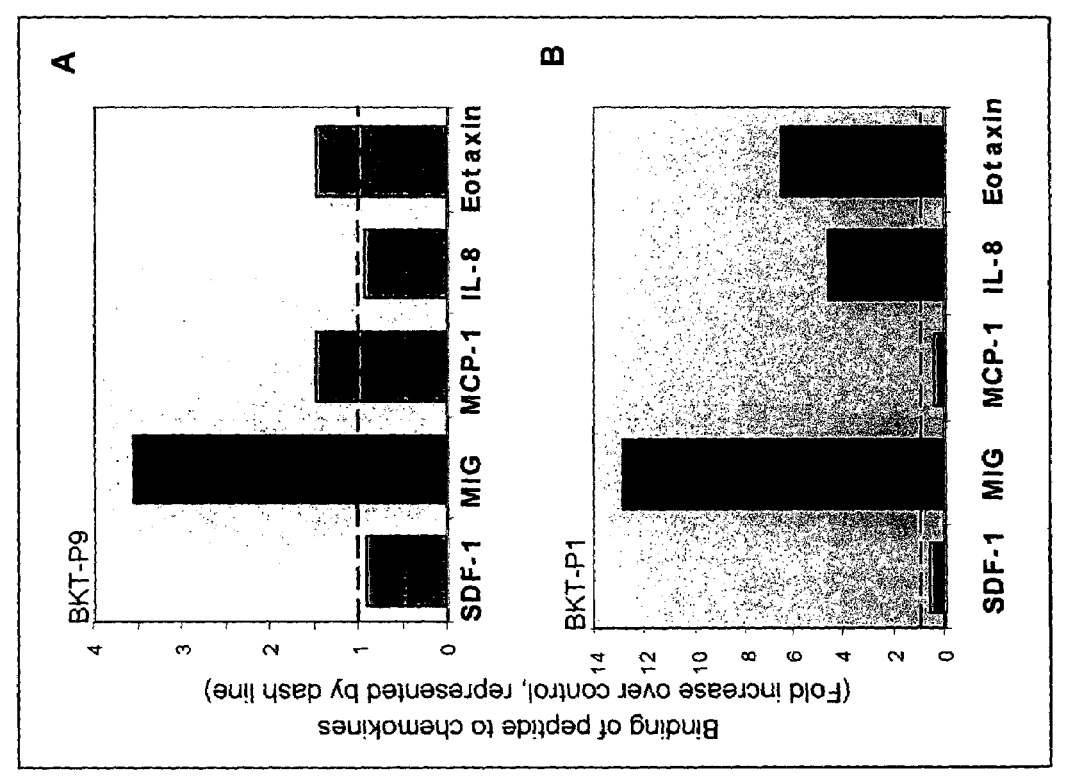

As can be seen in FIG. 2, peptides that can specifically bind to one specific chemokine, such as BKT-P9, were identified (FIG. 2A). In addition, peptides that can bind, specifically to more than one chemokine, such as BKT-P1, were also identified (FIG. 2B). Again, the specificity of the binding, either to one chemokine or more, was established by comparing binding level with the control binding level to non-related proteins, (shown in the Figure as a broken line). Control binding showed a level of one fold increase. As such, each of the peptides that showed a level of binding to a particular chemokine of less than, or close to, such a one-fold increase, was considered to be non-specifically bound to that chemokine. Specific binding was considered as that which showed at least a two fold increase over the control binding level. Peptides that specifically bound to one or more chemokines were chosen for further examination and for analysis with a biovalidation assay, to prove their ability to not only bind the various chemokines but also to modulate the biological activity of those chemokines.

According to the present invention, two families of chemokine-binding peptides were identified. These families contain peptides with similar amino acid compositions, a high percentage of histidines, and are also characterized by overall positive electrostatic charge.

A detailed list of the potential consensus sequences of the two families is presented in Tables 2 and 3. The peptides of family no. 1 (Table 2) bind to MIG, MCP-1, IL-8, SDF-1α and Eotaxin, as illustrated in Table 2, and are predominantly composed of the amino acids H, S, A, L, I, K, R, T and P. Each peptide in this family contains at least 2 histidines distributed along the molecule. The abundance of positively charged amino acids such as H, K and R, results in peptides having an overall positive charge. The remaining amino acids, mentioned above, might participate in the determination of the three dimensional structure of the peptides.

Table 3 shows a family of peptides (family no. 2) that bind mostly to MCP-1 and in individual cases to IL-8, SDF-1α and Eotaxin (illustrated in the Table). The binding motif for peptides in this family is predominantly composed of the amino acids H, P, T, L, R, W, F, while each peptide also features at least two histidines, one next to the other. The abundance of positively charged amino acids such as H and R, resulted in peptides having an overall positive charge; The remaining amino acids, mentioned above, may participate in the determination of the three dimensional structure of the peptides.

As defined here, a consensus sequence is composed of an amino acid sequence that is found repeatedly in a group of peptides that bind various chemokines and probably have certain biological functions in common. The group or family of such peptides is characterized by the consensus sequence, high abundance of the amino acid histidine and overall positive electrostatic charge. These peptides may be described as potential agonists or antagonists of chemokines.

Figure 3:
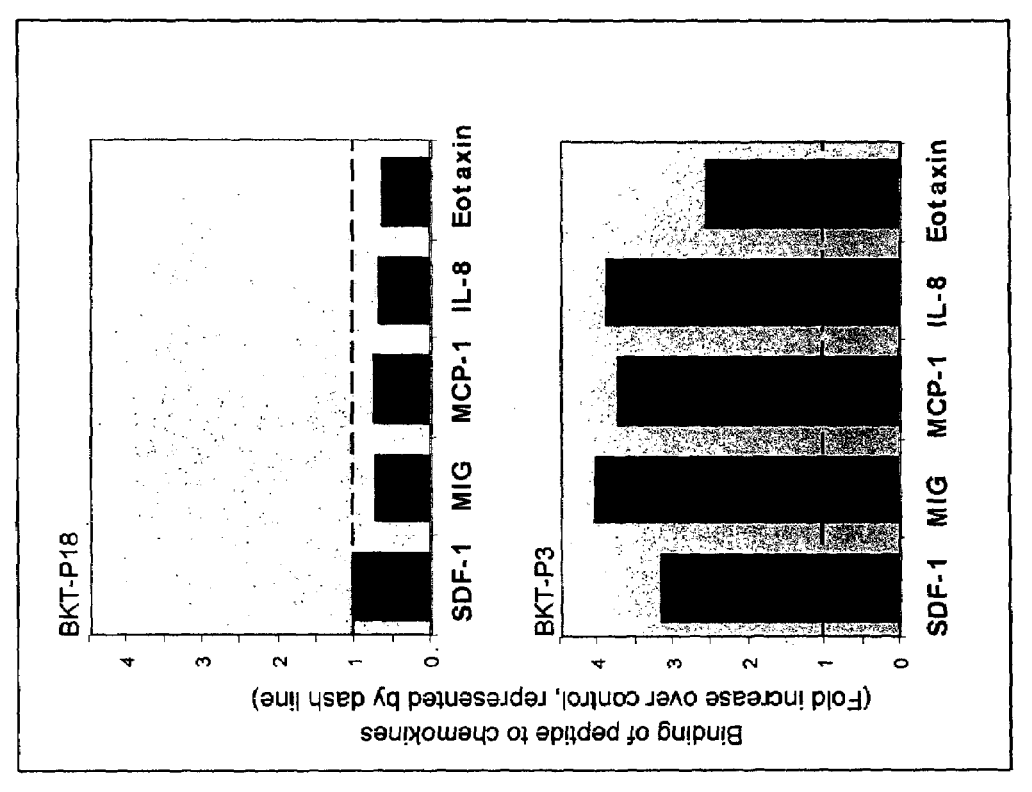

The binding of one synthetic peptide, BKT-P3 (family 1), to various chemokines is shown in FIG. 3. As can be seen, this peptide binds to all five chemokines tested, in contrast to the control peptide, BKT-P18, which does not belong to the family, and also shows no binding to the chemokines. As discussed above, the level of binding was calculated by comparing binding of the peptides to the chemokines with peptide binding to controls. Level of control binding was defined as level 1 (up to a one-fold increase in binding). This control binding level is illustrated in the Figure as a dashed line. It can be seen that although BKT-P3 binds several different chemokines, the level of the binding is different in each case, which suggests different affinities and maybe different influences on the activity of each of the chemokines.

Further examination of BKT-P3 for efficacy in biovalidation was performed to check the ability of BKT-P3 to bind and modulate the activity of MIG chemokine, to which BKT-P3 showed the highest binding level (FIG. 3). The result of the experiment is graphically illustrated in FIG. 4.

As can be seen in FIG. 4B, when a control peptide (which does not belong to family 1 and which also does not bind to the chemokine being examined (MIG)) was added to the flow chamber in order to test for its ability to bind to and modulate the activity of MIG, no influence on the activity of MIG was seen. MIG activity continued to show the same level of activity (about 25%-30% of arrested cells) as was seen in the absence of peptide. Hence, as can be seen in FIG. 4B, the same percentage of arrested cells could be detected in the presence of the chemokine, with or without the addition of BKT-P10 (the control peptide) (FIG. 4B, Mig+p10 and Mig, respectively). On the other hand, when BKT-P3, which was previously found to bind MIG chemokine, was added to the flow chamber, the percentage of arrested cells that reached about 25-30% in the presence of Mig (FIG. 4A, Mig), was dramatically reduced (FIG. 4A, Mig+p3) to the control level, achieved in the presence of VCAM-1 alone, with no addition of chemokine (FIG. 4A, control). These results revealed an obvious antagonistic effect of BKT-P3 against human MIG, the chemokine to which it was able to bind (FIG. 4A), in contrast to the non-binding control peptide, BKT-P10 (FIG. 4B).

Table 4 shows a summary of the biological activity results for four representative synthetic peptides belonging to family 1. Various different chemokines were used in the biovalidation assay together with the adhesion receptor VCAM-1, in order to activate the adhesion of T cells in the system (as described in "Materials and Methods"). As can be seen in Table 4, all the peptides that were checked clearly showed antagonistic effect on the various chemokines that were introduced into the flow chamber. On the other hand, although all the peptides showed antagonistic effects, the efficiency of the effect varied between the different peptides and between the same peptides tested against different chemokines. Thus, BKT-P3 caused complete arrest of the biological activity of both chemokines that were checked, MIG and IL-8. BKT-P2, which shows high sequence similarity to BKT-P3, caused only about 50% reduction in the activity of MIG. BKT-P45, which caused 100% abolishment of the activity of IL-8, as did BKT-P3, only reduced the activity of MIG by about 20%. BKT-P39, on the other hand, which had no effect on IL-8, caused 100% blocking of the activity of Eotaxin. It therefore seems that although the sequence similarity between the members of the family is quite high, and causes similar biological activity (antagonistic activity), the particular order of specific significant residues within the peptide sequence is also important.

Table 5 shows a summary of the biological activity results for two representative synthetic peptides listed in Table 1, neither of which belong to the previously described families (family 1 and family 2). As described in the previous experiment, various different chemokines were used in the biovalidation assay, together with the adhesion receptor VCAM-1, in order to activate the adhesion of T cells in the system (as described in "Materials and Methods"). As can be seen in Table 5, each of the tested peptides showed entirely different behavior. While BKT-p23 showed an antagonistic effect with two of the four chemokines that it was allowed to bind, although at different efficiencies, BKT-P6 showed an obvious agonistic effect on SDF1α, while having no effect on MIG activity. BKT-P23 blocks 100% of Eotaxin activity but only about 20% of the activity of SDF-1α, and has no effect on the activity of either IL-8 or MIG. BKT-P6 enhances SDF-1α activity by at least twenty fold, and has no effect on MIG activity. It therefore appears, that although there is only slight sequence similarity between BKT-P23 and the members of families 1 and 2, the fact that this peptide carries an overall positive charge, as do the members of families 1 and 2, probably contributes to its ability to act as an antagonist of various chemokines, thereby somewhat resembling the activity of the members of the two families (BKT-P39 for example). On the other hand, BKT-P6 acts as an agonist. This peptide is a circular peptide and differs in its sequence composition, compared to the two families. BKT-P6 is a highly polar molecule, and this property, as well as its circular configuration and the resulting 3D structure, may contribute to its activity.

It is also important to note that this peptide (BKT-P6) was the first chemokine agonist to be identified. Such agonists could clearly be important for a number of different reasons. For example, a designed chemokine agonist, whether in peptide form and/or a peptide derivative (eg with one or more chemical bonds substituted and/or other molecules substituted for one or more amino acids), could be useful in combination with other chemokines, for synergistic treatment, and/or as a substitute for a chemokine in a therapeutic situation in which the chemokine has a desired effect on the subject. For example, pre clinical studies have shown that MCP-1 is a powerful stimulator of vessel formation. This chemokine is in advanced stages of development for clinical use in restenosis. Augmenting the activity of MCP-1 may lead to better outcome of therapy.

As another example, HCV (herpes cytomegalovirus) infection is resolved by the immune system in only 20% of cases, while the other 80% of cases developed chronic disease which may lead to a requirement for liver transplantation and/or liver cancer, such as hepatocellular carcinoma. Augmenting the activity of chemokines such as Mig and IP-10, which participate in the regulation of the immune response against HCV, may also lead to better outcome of therapy in this situation.

Further examination of BKT-P3 and BKT-P2 (both belonging to family 1) for the immunity of these peptides was performed, by injecting those peptides to mice. The result of the experiment is graphically illustrated in FIG. 5. The control, pre-immune serum of the same mice to which the peptides were injected showed no binding to the two peptides (the O.D. results of both pre-immune sera were the same as the O.D. achieved by binding of all sera to the plastic with no peptide addition). On the other hand, the immune sera showed high O.D. levels, in the presence of the two peptides. These results showed that the sera collected from the mice after injection of the peptides contain antibodies against the two peptides.

The results summarized above are very important, since it is known that one chemokine can bind to more than one receptor and as such, can be involved in more than one pathological disorder. On the other hand, more then one chemokine can bind to one receptor, which means that several chemokines might be involved in one pathological disorder. So, in some cases, in order to block one pathological disorder, it may be necessary to block the activity induced by more than one chemokine. Alternatively, in some cases, the activity of only one specific chemokine may need to be blocked in order to interfere with the progression of one specific pathological disorder.

The results, shown in FIGS. 2 and 3, and Tables 4 and 5, demonstrate that there is a possibility of modulating either the activity of one specific chemokine, or the activity of-several different chemokines that are involved in the development of one pathological disorder, and thereby interfering with the progression of the various diseases.

The results shown in FIG. 5 demonstrate the immunogenicity of the peptides. The ability to raise antibodies against the peptides, which would therefore mimic the chemokine receptors, provides support to other applications of the present invention, including but not limited to, the development of vaccines against the chemokine receptors. These receptors are known to be involved in various pathological disorders. Such vaccines would thus enable treatment and/or prevention of such disorders.

EXAMPLE 2

Efficacy of the Peptides of the Present Invention

This Example demonstrates the efficacy of the peptidic chemokine-binding modulators of the present invention, in a number of different assays, including binding assays and assays for measuring a functional biological effect both in vitro and in vivo.

Materials and Methods

Chemokines

Recombinant chemokines were ordered from PeproTech, Inc. (Rocky Hill, N.J. USA). Human SDF-1α (Cat. No. 300-28A), human MIG (Cat. No. 300-26) and human IL-8, (72 amino acids) (Cat. No. 200-08M), belong to the alpha-chemokines (C-X-C) family. Human MCP-1 (MCAF) (Cat. No. 300-04) and human Eotaxin (Cat No. 300-21) belong to the beta-chemokines (C-C family). All chemokines were prepared according to the company recommendations.

Peptide Synthesis

Synthetic peptides were ordered from BioSight Ltd, Karmiel, Israel, in order to perform tests for characterization of their influence on the biological activity of the chemokines. The format of the various synthesized peptides was as follows: The cyclic peptides, $ACX_7CGGGSK$-biotin-G and the linear peptides, $X_{12}GGGSK$-biotin-G. The peptides were biotinylated on their C-termini; the biotin serves as a detector during the following experiments. Each synthetic peptide is dissolved to concentration of 1 mg/ml (~0.6 mM) in 4% DMSO (Dimethyl Sulphoxide, Sigma, Cat. # D-2650).

ELISA Analysis of the Synthetic Chemokine-Binding Peptide

NUNC-Immuno maxisorp plates (Cat. No. 4-42404) are coated with the appropriate chemokine (0.1 ml/well, 0.1-1.0 µg/ml in 0.1 M $NaHCO_3$, pH 8.6), overnight at 4° C. The plates are then blocked with 0.2 ml/well of blocking buffer (5 mg/ml BSA in 0.1 $NaHCO_3$). Control wells are treated with blocking buffer alone, with no addition of target protein (chemokine). The plates are washed 6 times with PBST (0.1% TWEEN®20 (polyoxyethylene (20) sorbitan monolaurate) in PBS), followed by incubation for 45 minutes at room temperature with 10-fold serial dilutions of individual synthetic peptides (10 pg-10µg) with 1%BSA (PBST-BSA)/well. After the plates are washed 6 times with PBST, the bound peptides are probed by HRP-SA Conjugate, diluted 1:10,000 to 1:20,000 in PBST-BSA, 0.1 ml/well for 45 minutes at room temperature. The target-bound synthetic peptides probed with HRP-SA are quantified by DAKO TMB one-step substrate system, followed by the addition of stop solution, HCl-$H_2SO_4$ mixture (0.1 ml/well) (1N HCl, 3N $H_2SO_4$). The results are analyzed by ELISA reader at $OD_{450}$.

T-Cell Purification from Fresh Blood 50 ml blood is added to 10 ml Dextran (Dextran T-500 6% m/v) in PBS (phosphate buffer saline), and 7 ml Citrate buffer (25 g citrate, 8 g citric acid in 500 ml PBS). The solution is incubated for 30 min at 25° C. 10 ml Ficoll 1077 (sigma) is added to the bottom of the tube. The tube is then centrifuged at 2,000 rpm for 30 min, at 18° C., (with the brake mode of the centrifuge off). The interphase was collected and washed twice with 8 ml PBS-5% FCS (fetal calf serum) followed by centrifugation at 1,400 rpm, for 5 min, at 18° C. The cells are re-suspended in PBS-5% FCS at a concentration less then $10^8$/ml. 2 ml of the cells solution are applied and incubated for 45 min at 25° C. on a Perspex Nylon wool column, which is pre-soaked with PBS-5% FCS. Each column is washed with 8 ml PBS-5% FCS and the cells (T-cells and erythrocytes) are eluted by 50 ml of 5 mM EDTA in PBS. A red pellet is obtained by centrifugation at 1,400 rpm, at 4° C., for 5 min, with the brake on. In order to perform lysis of the erythrocytes, the red pellet is re-suspended in 5 ml lysis-buffer (155 mM $NH_4Cl$, 10 mM $KHCO_3$, 0.1 mM EDTA, X0.1PBS) for 4 min, followed by immediate addition of 50 ml of PBS-EDTA. Following centrifugation at 1,400 rpm, at 4° C., for 5 min with brake on, the pellet is washed again with 50 ml PBS-EDTA and re-centrifuged under the same conditions. A white pellet is obtained and re-suspended in RPMI/10% FCS/L-glutamine/sodium pyruvate/antibiotics at a concentration of $3^x 10^6$ cells/ml. The cells are incubated for 2 h at 37° C., followed by collecting of the non-adherent cells. The cells are ready for experiments after overnight incubation at 37° C.

Preparation of Adhesive Substrates

Human VCAM-1 (1 μg/ml) and SDF-1α (intact or heat-inactivated) (2 μg/ml) are dissolved in PBS buffered with 20 mM bicarbonate, pH 8.5, and incubated on a polystyrene plates overnight at 4° C. The plates are then washed three times and blocked with human serum albumin (20 mg/ml in PBS) for 2 h at 37° C.

Biovalidation

Laminar flow assays are performed as follows. Polystyrene plates (B.D) are coated with soluble VCAM-1 at 10 μg/ml in the presence of 2 μg/ml HSA carrier. The plates are washed three times with PBS and blocked with HSA (20 μg/ml in PBS) for 2 hrs at room temperature. Alternatively, wound plates are coated with 10 μg/ml MIG chemokine in PBS for 30 min at room temperature, before being blocked with HSA. The plates are assembled as the lower wall of a parallel wall flow chamber and mounted on the stage of an inverted microscope. The peptide, as described previously, (10 μg/ml) is allowed to settle on the substrate coated chamber wall for 10 min, at 37° C. and then washed. T cells ($5\times10^6$/ml, purity >98% ) are suspended in binding buffer, perfused into the chamber and allowed to settle on the substrate coated chamber wall for 1 min, at 37° C. Flow is initiated and increased in 2 to 2.5 fold increments every 5 sec. generating controlled shear stresses on the wall. Cells are visualized in a 20x objective of Nikon DIAPHOT TMD Biological Inverted Microscope (Nikon, Japan) and photographed with a long integration LIS-700 CCD video camera (Applitech; Holon, Israel), connected to a video recorder (AG-6730 S-VHS, Panasonic, Japan). The number of adherent cells resisting detachment by the elevated shear forces is determined after each interval by analysis of videotaped cell images, and is expressed as the percent of originally settled cells. All adhesion experiments are performed -at least three times on multiple test fields.

In-Vitro Migration Assay

The migration of purified T cells in vitro towards chemokines is determined by a trans-well migration. The cells are viewed in an inverted microscope, before starting the procedure. Following centrifugation of the cells at 1,300 rpm, for 5 min, at R.T., the cells are re-suspended in RPMI/1% FCS for a concentration of $1.8^x 10^6$ cells /ml. In parallel, the transwells (Costar 3421, Corning Costar, Cambridge, MA) are coated with 100μl of fibronetcin, 10μg/ml for 1 hr at 37° C. Subsequently, 100 μl of the treated cells are added to the upper chamber of the trans-well, and 600 82 l of RPMI+1% FCS is added to the lower chamber of the transwell, with or without 100 ng/ml chemokine to be checked, with or without various concentrations of the peptide to be checked . The experiment is performed in triplicates. The incubation takes place for 4 h or 5 h at 37° C. Following staining with Trypan-blue or Alamar +, the cells in the lower chamber of the trans-well are counted, by FACS, cell counter or fluorometer, respectively. The percentage of migration is calculated as the percent of migrated cell (minus the background), from the total number of the cells that are loaded on the trans-well. Percentage of migration inhibition is calculated as the percentage of migration in the presence of the peptides compared to the migration of cells subjected to the same treatment, in the absence of the peptides.

In Vivo Migration Assay

Wild-type (WT) male BALB/c mice (18-25 g), with age ranging between 8 and 12 weeks, are used throughout these experiments. Animals are fed commercial rodent chow and are housed in a temperature-controlled room with free access to water and food.

The migration of Eosinophils or Neutrophils in vivo to the peritoneum, in response to various chemokines, is determined by injection of the chemokine to be checked, with or without (control) the peptide in question, i.v. into the peritoneum of the mice. The animals are sacrificed at different times after the injection and their peritoneal cavities are washed with 2-4 ml of PBS and the total cell counts are determined.

Results

Peptide Synthesis

Eight different peptides were purchased (Table 6). The peptides to be ordered were determined as previously described. BKT-P3 was ordered as a 12 amino acid peptide, without the linker (discussed in "Materials and Methods"). The peptide had previously been found to be effective in this configuration, and will be used in both in vivo experiments and Abs production. BKT-P2 and BKT-P39, which belong to family 1, were ordered for further studies, since, in spite of their resemblance to BKT-P3, they are effective at promoting activities related to chemokines other than those for which BKT-P3 is effective. BKT-P49, which also belongs to family 1, was ordered as a cyclic representative of family 1. The rest of the peptides that were ordered, are peptides that do not belong to family 1 and were ordered as such. The other two peptides, BKT-P35 and 57 were chosen as representatives of linear and circular peptides that do not belong to the recognized families. The last peptide, BKT-P 18, is a control peptide, which showed no binding to the various chemokines and was used as such. All the ordered peptides are checked for their ability to bind the various chemokines and modulate their activity, both in vitro and in vivo, as per the previously described experiments.

EXAMPLE 3

Methods and Compositions for Administration

The peptides of the present invention, and their homologues, derivatives or related compounds, hereinafter referred to as the "therapeutic agents of the present invention", can be administered to a subject by various ways, which are well known in the art. Hereinafter, the term "therapeutic agent" includes a peptidic chemokine-binding modulator, as previously defined, including but not limited to, any of the above biologically useful peptides and their homologs, analogs, peptidomimetics and derivatives thereof.

Hereinafter, the term "subject" refers to the human or lower animal to which the therapeutic agent is administered For example, administration may be done topically (including ophthalmically, vaginally, rectally, intranasally and by inhalation), orally, or parenterally, for example by intravenous drip or intraperitoneal, subcutaneous, or intramuscular injection.

Formulations for topical administration may be included but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions, which may also contain buffers, diluents and other suitable additives.

Dosing is dependent on the severity of the symptoms and on the responsiveness of the subject to the therapeutic agent. Persons of ordinary skill in the art can easily determine optimum dosages, dosing methodologies and repetition rates.

EXAMPLE 4

Methods of Treatment with the Compounds

As noted above, the therapeutic agents of the present invention have been shown to be effective modulators of cell adhesion and cell migration that characterize inflammatory reaction, cancer metastasis and any other suitable conditions in which a particular target ligand binds to its target receptor. The following example is an illustration only of a method of treating an inflammatory condition, cancer metastasis and any other suitable condition involving cell migration, with the therapeutic agent of the present invention, and is not intended to be limiting.

The method includes the step of administering a therapeutic agent, in a pharmaceutically acceptable carrier, to a subject to be treated. The therapeutic agent is administered according to an effective dosing methodology, preferably until a predefined endpoint is reached, such as the absence of a symptom of the inflammatory condition, blockage of tumor metastasis and any other suitable condition in the subject, or the prevention of the appearance of such a condition or symptom in the subject.

The modulatory chemokine-binding peptide molecules of the present invention could therefore be useful for treating a disease selected from the group consisting of inflammation (primary or secondary e.g. uveitis, bowel inflammation), allergy, non-optimal immune response, autoimmune reaction (including rheumatoid arthritis, systemic lupus erythematosis, multiple sclerosis and others), delayed-type hypersensitivity, allograft rejection, diabetes, sepsis, cancer and any type of malignant cell growth, (including, but not limited to breast cancers such as infiltrating duct carcinoma of the breast or other metastatic breast cancers, lung cancers such as small cell lung carcinoma, bone cancers, bladder cancers such as bladder carcinoma, rhabdomyosarcoma, angiosarcoma, adenocarcinoma of the colon, prostate or pancreas, or other metastatic prostate or colon cancers, squamous cell carcinoma of the cervix, ovarian cancer, malignant fibrous histiocytoma, skin cancers such as malignant melanoma, lymphomas and leukemia, leiomyosarcoma, astrocytoma, glioma and heptocellular carcinoma), acute and chronic bacterial and viral infections, vasculitis, arthritis, colitis, psoriasis, atherosclerosis, Graves disease, anorexia nervosa; hemorrhagic shock caused by septicemia, HIV infection, pemphigus, asthma, renal diseases, liver diseases, bone marrow failure, vitiligo, alopecia, and myositis, hypertension and reperfusion ischemia.

EXAMPLE 5

Method of Immunization with the Peptides

This Example provides a non-limiting illustrative method according to the present invention for inducing an immune response in a subject with one or more of the peptides (or peptidomimetics, homologs, derivatives etc as previously described) according to the present invention. This method would preferably enable blockage of binding of a chemokine to its receptor, and/or immune sequestration of the receptor, by causing the immune system of the subject to produce an antibody against the receptor. Since the peptides according to the present invention bind chemokines, an antibody against such a peptide would be expected to bind to the receptor of the chemokine and/or to block binding of the chemokine to the receptor. In any case, such an immunization would be expected to block or at least reduce the biological activity induced by the receptor.

Examples of such methods with regard to another protein, the heparanase enzyme, are described in PCT Application No. WO 03/006645, hereby incorporated by reference as if fully described herein.

Briefly, the chemokine biological activity is inhibited by elicitation of an immune response to the peptide according to the present invention following administration of an effective amount of the peptide. In the context of the present invention, the peptide is administered in an amount effective to elicit an immune response, including a humoral or cell-mediated immune response, against the native receptor. The immune response is preferably an active immunity that inhibits, that is, prevents, slows, or stops, the chemokine-induced biological activity. Therefore, in the context of the present inventive methods, such biological activity need not be completely abrogated. It should be appreciated that the immune response against the receptor can be elicited either directly or indirectly.

In an alternative embodiment, the peptide of the present invention can be modified in various ways known to one of skill in the art, for example, by co-administering with or conjugating or genetically fusing it to an immunogenic reagent. Conjugation or fusion to an immunogenic reagent can stimulate an immune response or augment the existing immune response elicited by the peptide. These conjugates and fused molecules can be prepared by any of the known methods for coupling or fusing antigens to carriers or fusion molecules. The conjugates can also be prepared recombinantly as fusion polypeptides by methods well known in the art. The preferred method of conjugation is covalent coupling, whereby the antigen is bound directly to the immunogenic reagent. Moreover, coadministration can be such that the immunogenic reagent is administered prior to, concurrently with, or subsequent to the peptide.

While the invention has been described with respect to a limited number of embodiments, it will be appreciated that many variations, modifications and other applications of the invention may be made.

TABLE 1

| Peptide Name | Seq id no: | Sequence of peptide |
|---|---|---|
| BKT-P50 | 1 | CAHLSPHKC |
| BKT-P10 | 2 | CDIPWRNEC |
| BKT-P17 | 3 | CDPLRQHSC |
| BKT-P58 | 4 | CDSLGHWLC |
| BKT-P15 | 5 | CDYTTRHSC |
| BKT-P59 | 6 | CHGTLNPEC |
| BKT-P56 | 7 | CHHNLSWEC |
| BKT-P60 | 8 | CHIWTLASC |
| BKT-P61 | 9 | CHNTFSPRC |
| BKT-P62 | 10 | CIPLHASLC |
| BKT-P63 | 11 | CITTTSLSC |
| BKT-P64 | 12 | CKLTTCKDC |
| BKT-P65 | 13 | CKNHTTFWC |
| BKT-P66 | 14 | CLKLLSRSC |
| BKT-P67 | 15 | CLLKAHPSC |
| BKT-P68 | 16 | CLNQLKQAC |
| BKT-P69 | 17 | CMNFPSPHC |
| BKT-P70 | 18 | CPQSPTYTC |
| BKT-P57 | 19 | CPSSAIHTC |
| BKT-P71 | 20 | CPTSTARIC |
| BKT-P72 | 21 | CQASSFPSC |
| BKT-P73 | 22 | CQPYFWYRC |
| BKT-P14 | 23 | CQTLTPSIC |
| BKT-P74 | 24 | CSKLGHLWC |
| BKT-P75 | 25 | CSKTPERIX |
| BKT-P76 | 26 | CSNNNRMTC |
| BKT-P77 | 27 | CSPILSLSC |
| BKT-P16 | 28 | CSPTNFTRC |
| BKT-P78 | 29 | CSRPAMNVC |
| BKT-P79 | 30 | CSTKAYPNC |
| BKT-P80 | 31 | CSTSSCGSC |
| BKT-P81 | 32 | CSYWGHRDC |
| BKT-P13 | 33 | CTAHDANAC |
| BKT-P82 | 34 | CTANSEKTC |
| BKT-P83 | 35 | CTHPKASMC |
| BKT-P84 | 36 | CTKTINGKC |

TABLE 1-continued

| Peptide Name | Seq id no: | Sequence of peptide |
|---|---|---|
| BKT-P85 | 37 | CTNMQSPLC |
| BKT-P86 | 38 | CTPFTKLPC |
| BKT-P87 | 39 | CTPTTDSIC |
| BKT-P88 | 40 | CTQQNGHPC |
| BKT-P12 | 41 | ACTTPSKHQC |
| BKT-P89 | 42 | CTYNVAKPC |
| BKT-P90 | 43 | ACAPLMFSQC |
| BKT-P48 | 44 | ACHASLKHRC |
| BKT-P91 | 45 | AHFSPNLLLGG |
| BKT-P44 | 46 | AHSLKSITNHGL |
| BKT-P92 | 47 | AKTLMPSPFPRT |
| BKT-P93 | 48 | ASAVGSLSIRWQ/L/G |
| BKT-P94 | 49 | ASWVDSRQPSAA |
| BKT-P95 | 50 | CPQLTVGQHRT |
| BKT-P8 | 51 | DLPPTLHTTGSP |
| BKT-P96 | 52 | DSSNPIFWRPSS |
| BKT-P97 | 53 | EFLGVPASLVNP |
| BKT-P51 | 54 | ESDLTHALHWLG |
| BKT-P98 | 55 | EVHSTDRYRSIP |
| BKT-P99 | 56 | FGLQPTGDIARR |
| BKT-P9 | 57 | FSMDDPERVRSP |
| BKT-P100 | 58 | FSPLHTSTYRPS |
| BKT-P27 | 59 | GDFNSGHHTTTR |
| BKT-P28 | 60 | GPSNNLPWSNTP |
| BKT-P33 | 61 | GVHKHFYSRWLG |
| BKT-P101 | 62 | HAPLTRSPAPNL |
| BKT-P102 | 63 | HGSLTTLF/LRYEP |
| BKT-P45 | 64 | HHFHLPKLRPPV |
| BKT-P55 | 65 | HHTWDTRIWQAF |
| BKT-P54 | 66 | HPTTPFIHMPNF |
| BKT-P103 | 67 | HRDPXS(P)PSAA/GRP |
| BKT-P104 | 68 | HNVTTRTQRLMP |
| BKT-P49 | 69 | HSACHASLKHRC |
| BKT-P105 | 70 | HSACKLTTCKDG |
| BKT-P6 | 71 | HSACLSTKTNIC |
| BKT-P106 | 72 | IAHVPETRLAQM |
| BKT-P107 | 73 | IFSMGTALARPL |
| BKT-P108 | 74 | INKHPQQVSTLL |

TABLE 1-continued

| Peptide Name | Seq id no: | Sequence of peptide |
|---|---|---|
| BKT-P7 | 75 | ISPSHSQAQADL |
| BKT-P46 | 76 | LDYPIPQTVLHH |
| BKT-21 | 77 | LFAAVPSTQFFR |
| BKT-P22/38 | 78 | LGFDPTSTRFYT |
| BKT-P37 | 79 | LLADTTHHRPWP |
| BKT-P109 | 80 | LPWAPNLPDSTA |
| BKT-P110 | 81 | LQPSQPQRFAPT |
| BKT-P111 | 82 | LSPPMQLQPTYS |
| BKT-P112 | 83 | MHNVSDSNDSAI |
| BKT-P113 | 84 | NSSMLGMLPSSF |
| BKT-P114 | 85 | NTSSSQGTQRLG |
| BKT-P42 | 86 | PGQWPSSLTLYK |
| BKT-P23 | 87 | QIPQMRILHPYG |
| BKT-P24 | 88 | QIQKPPRTPPSL |
| BKT-P115 | 89 | QLTQTMWKDTTL |
| BKT-P116 | 90 | QNLPPERYSEAT |
| BKT-P117 | 91 | QSLSFAGPPAWQ |
| BKT-P118 | 92 | QTTMTPLWPSFS |
| BKT-P119 | 93 | RCMSEVISFNCP |
| BKT-P120 | 94 | RSPYYNKWSSKF |
| BKT-P39 | 95 | SAGHIHEAHRPL |
| BKT-P40 | 96 | SAISDHRAHRSH |
| BKT-P121 | 97 | SEPTYWRPNMSG |
| BKT-P32 | 98 | SFAPDIKYPVPS |
| BKT-P31 | 99 | SFWHHHSPRSPL |
| BKT-P3 | 100 | SIFAHQTPTHKN |
| BKT-P2 | 101 | SIPSHSIHSAKA |
| BKT-P122 | 102 | SIRTSMNPPNLL |
| BKT-P123 | 103 | SLPHYIDNPFRQ |
| BKT-P29 | 104 | SLSKANILHLYG |
| BKT-P124 | 105 | SLVTADASFTPS |
| BKT-P125 | 106 | SMVYGNRLPSAL |
| BKT-P126 | 107 | SPSLMARSSPYW |
| BKT-P127 | 108 | SPNLPWSKLSAY |
| BKT-P1 | 109 | SQTLPYSNAPSP |
| BKT-P128 | 110 | SSTQAHPFAPQL |
| BKT-P129 | 111 | STPNSYSLPQAR |
| BKT-P4 | 112 | STVVMQPPPRPA |

TABLE 1-continued

| Peptide Name | Seq id no: | Sequence of peptide |
|---|---|---|
| BKT-P34 | 113 | SVQTRPLFHSHF |
| BKT-P130 | 114 | SVSVGMKPSPRP |
| BKT-P131 | 115 | SYIDSMVPSTQT |
| BKT-P132 | 116 | SYKTTDSDTSPL |
| BKT-P133 | 117 | TAAASNLRAVPP |
| BKT-P5 | 118 | TAPLSHPPRPGA |
| BKT-P134 | 119 | TGLLPNSSGAGI |
| BKT-P135 | 120 | TGPPSRQPAPLH |
| BKT-P30 | 121 | TLSNGHRYLELL |
| BKT-P25 | 122 | TPSPKLLQVFQA |
| BKT-P136 | 123 | TPSTGLGMSPAV |
| BKT-P137 | 124 | TPVYSLKLGPWP |
| BKT-P47 | 125 | TRLVPSRYYHHP |
| BKT-P138 | 126 | TSPIPQMRTVPP |
| BKT-P139 | 127 | TTNSSMTMQLQR |
| BKT-P140 | 128 | TTTLPVQPTLRN |
| BKT-P141 | 129 | TTTWTTTARWPL |
| BKT-P142 | 130 | TVAQMPPHWQLT |
| BKT-P143 | 131 | TWNSNSTQYGNR |
| BKT-P144 | 132 | TWTLPAMHPRPA |
| BKT-P26 | 133 | VHTSLLQKHPLP |
| BKT-P35 | 134 | VLPNIYMTLSA |
| BKT-P145 | 135 | VMDFASPAHVLP |
| BKT-P146 | 136 | VNQEYWFFPRRP |
| BKT-P147 | 137 | VYSSPLSQLPR |
| BKT-P148 | 138 | VPPIS(R)TFLF(L)ST(K)S |
| BKT-P149 | 139 | VPPLHPALSRXN |
| BKT-P43 | 140 | VSPFLSPTPLLF |
| BKT-P150 | 141 | VSRLGTPSMHPS |
| BKT-P151 | 142 | WPFNHFPWWNVP |
| BKT-P52 | 143 | WSAHIVPYSHKP |
| BKT-P152 | 144 | WWPNSLNWVPRP |
| BKT-P53 | 145 | YATQHNWRLKHE |
| BKT-P153 | 146 | YCPMRLCTDC |
| BKT-P154 | 149 | YGKGFSPYFHVT |
| BKT-P155 | 148 | YPHYSLPGSSTL |
| BKT-P156 | 149 | YPSLLKMQPQFS |
| BKT-P157 | 150 | YQPRPFVTTSPM |

TABLE 1-continued

| Peptide Name | Seq id no: | Sequence of peptide |
|---|---|---|
| BKT-P158 | 151 | YSAPLARSNVVM |
| BKT-P36 | 152 | YTRLSHNPYTLS |
| BKT-P41 | 153 | YTTHVLPFAPSS |
| BKT-P159 | 154 | YTWQTIREQYEM |
| BKT-P6 | 155 | CLSTKTNIC |
| BKT-P6 | 156 | ACLSTKTNIC |
| BKT-P11 | 157 | CTTPSKHQC |

TABLE 2

| Peptide name | Seq id no: | Peptide sequence | Bound chemokines (at least) |
|---|---|---|---|
| BKT-P3 | 100 | SIFAHQTPTHKN | MIG, IL-8, MCP-1 |
| BKT-P2 | 101 | SIPSHSIHSAKA | MCP-1, Eotaxin, IL-8 |
| BKT-P40 | 96 | SAISDHRAHRSH | IL-8 |
| BKT-P39 | 95 | SAGHIHEAHRPL | Eotaxin, SDF-1alpha, IL-8 |
| BKT-P48 | 44 | ACHASLKHRC | MCP-1 |
| BKT-P44 | 46 | AHSLKSITNHGL | MCP-1 |
| BKT-P51 | 54 | ESDLTHALHWL | MCP-1 |
| BKT-P49 | 69 | HSACHASLKHR | MCP-1 |
| BKT-P52 | 143 | WSAHIVPYSHKP | MCP-1 |
| BKT-P53 | 145 | YATOHNWRLKHE | MCP-1 |
| BKT-P50 | 1 | CAHLSPHKC | MIG |
| BKT-P33 | 61 | GVHKHFYSRWLG | Eotaxin |
| BKT-P54 | 66 | HPTTPFIHMPNF | MIG |
| BKT-P34 | 113 | SVQTRPLFHSHF | Eotaxin |
| BKT-P26 | 133 | VRTSLLQKHPLP | MCP-1 |

Amino Acid Composition
H = 33
S = 22
A = 16
L = 15
I = 7
K = 10
R = 8
T = 9
P = 12
N = 3
G = 3
W = 4
Y = 3
V = 3
E = 1
Q = 3
O = 1
D = 2

TABLE 3

| Peptide name | Seq id no: | Peptide sequence | Bound chemokines (at least) |
|---|---|---|---|
| BKT-P27 | 59 | GDFNSGHHTTTR | MCP-1 |
| BKT-P45 | 64 | HHFHLPKLRPPV | IL-8, MCP-1, MIG |
| BKT-P55 | 65 | HHTWDTRIWQAF | MCP-1 |
| BKT-P46 | 76 | LDYPIPQTVLHH | MCP-1 |
| BKT-P37 | 79 | LLADTTHHRPWP | IL-8 |
| BKT-P47 | 125 | TRLVPSRYYHHP | MCP-1 |
| BKT-P56 | 7 | CHHNLSWEC | SDF-1alpha |
| BKT-P31 | 99 | SFWHHHSPRSSPL | Eotaxin |

Amino Acid Composition
H = 18
P = 11
T = 9
L = 9
R = 6
W = 5
F = 4
D = 4
G = 2
N = 1
S = 7
K = 1
V = 2
I = 2
Q = 1
Y = 2
A = 2

TABLE 4

Families 1 and 2 Biovalidation Results

| Peptide name | Seq id no: | Peptide Sequence | Chemokine checked | Level of Antagonistic Effect |
|---|---|---|---|---|
| BKT-P3 | 100 | SIFAHQTPTHKN | MIG | +++ |
| | | | IL-8 | +++ |
| BKT-P2 | 101 | SIPSHSIHSAKA | MIG | ++ |
| BKT-P45 | 64 | HHFHLPKLRPPV | IL-8 | +++ |
| | | | MIG | + |
| BKT-P39 | 95 | SAGHIHEAHRPL | Eotaxin | +++ |
| | | | IL-8 | − |

Legend: The percentage of antagonistic effect is as follows:
+ 20%
++ 50%
+++ 100%
− No effect

TABLE 5

Non-family members Biovalidation Results

| Peptide name | Seq id no: | Peptide Sequence | Chemokine checked | Level of Effect | Kind of Effect |
|---|---|---|---|---|---|
| BKT-P23 | 87 | QIPQMRILHPYG | EOTAXIN | +++ | Antagonist |
|  |  |  | IL-8 | − |  |
|  |  |  | SDF-1α | + | Antagonist |
| BKT-P6 | 71 | HSACLSTKTNIC | MIG | − |  |
|  |  |  | SDF-1α | +++ | Agonist |

Legend: The percentage of modulatory effect is as follows:
+ 20%
++ 50%
+++ 100%
− No effect

TABLE 6

Synthetic peptides ordered

| Peptide name | Seq id no: | Peptide Sequence | Chemokines checked |
|---|---|---|---|
| BKT-P3 | 100 | SIFAHQTPTHKN | MIG IL-8 |
| BKT-P2 | 101 | SIPSHSIHSAKA | MCP-1 EOTAXIN IL-8 |
| BKT-P39 | 95 | SAGHIHEAHRPL | Eotaxin IL-8 |
| BKT-P49 | 69 | HSACHASLKHRC | − |
| BKT-P6 | 71 | HSACLSTKTNIC | MIG SDF-1α |
| BKT-P35 | 134 | VLPNIYMTLSA | − |
| BKT-P57 | 19 | CPSSAIHTC | − |
| BKT-P18 | − | CKESATYFC | − |

REFERENCES

Baggiolini, M., and C. A. Dahinden. 1994. Immunol. Today, 15, 127-133.

Cocchi, F., Devico, A. L., Garzino-Demo, A., Arya, S. K., Gallo, R. C. and P. Lusso. 1995. Science, 270, 1811-1815.

Ma, Q., Jones, D., Borghesani, P. R., Segal, R. A., Nagasawa, T., Kishimoto, T., Bronson, R. T. and T. A. Springer. 1998. Proc. Natl. Acad. Sci. USA, 95, 9448-9453.

Strieter, R. M., Polverini, P. J., Kunkel, S. L., Arenberg, D. A., Burdick, M. D., Kasper, J., Dzuiba, J., Van Damme, J., Walz, A., Marriott, D., et al. 1995. J. Biol. Chem., 270, 27348-27357.

Vaddi, K, and R. C. Newton. 1994. J. Immunol., 153, 4721-4732.

Muller A, Homey B, Soto H, Ge N, Catron D, Buchanan M E, McClanahan T, Murphy E, Yuan W, Wagner S N, Barrera J L, Mohar A, Verastegui E, Zlotnik A. 2001. Nature 410, 50-56.

What is claimed is:

1. A method of inhibiting a binding of a chemokine to a chemokine receptor, wherein said chemokine is selected from the group consisting of MCP-1 (monocyte chemotactic protein-1) and MIG (monokine induced by gamma interferon), the method comprising contacting the chemokine with an effective amount of a peptide comprising the amino acid sequence as set forth in SEQ ID NO:76.

2. The method of claim 1, wherein said peptide binds to at least one of said chemokines and directly inhibits a biological activity of said chemokine by inhibition of binding of said chemokine to said chemokine receptor.

3. A method of inhibiting a binding of a chemokine to a chemokine receptor, wherein said chemokine is selected from the group consisting of IL-8 (interleukin-8) and MIG, the method comprising contacting the chemokine with an effective amount of a peptide comprising the amino acid sequence as set forth in SEQ ID NO:64.

4. The method of claim 3, wherein said peptide binds to at least one of said chemokines and directly inhibits a biological activity of said chemokine by inhibition of binding of said chemokine to said chemokine receptor.

* * * * *

SEQUENCE LISTING

```
<160> NUMBER OF SEQ ID NOS: 157

<210> SEQ ID NO 1
<211> LENGTH: 9
<212> TYPE: PRT
<213> ORGANISM: Artificial sequence
<220> FEATURE:
<223> OTHER INFORMATION: Synthetic peptide

<400> SEQUENCE: 1

Cys Ala His Leu Ser Pro His Lys Cys
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic peptide

<400> SEQUENCE: 2

Cys Asp Ile Pro Trp Arg Asn Glu Cys
1               5

<210> SEQ ID NO 3
<211> LENGTH: 9
```

```
<212> TYPE: PRT
<213> ORGANISM: Artificial sequence
<220> FEATURE:
<223> OTHER INFORMATION: Synthetic peptide

<400> SEQUENCE: 3

Cys Asp Pro Leu Arg Gln His Ser Cys
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic peptide

<400> SEQUENCE: 4

Cys Asp Ser Leu Gly His Trp Leu Cys
1               5

<210> SEQ ID NO 5
<211> LENGTH: 9
<212> TYPE: PRT
<213> ORGANISM: Artificial sequence
<220> FEATURE:
<223> OTHER INFORMATION: Synthetic peptide

<400> SEQUENCE: 5

Cys Asp Tyr Thr Thr Arg His Ser Cys
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic peptide

<400> SEQUENCE: 6

Cys His Gly Thr Leu Asn Pro Glu Cys
1               5

<210> SEQ ID NO 7
<211> LENGTH: 9
<212> TYPE: PRT
<213> ORGANISM: Artificial sequence
<220> FEATURE:
<223> OTHER INFORMATION: Synthetic peptide

<400> SEQUENCE: 7

Cys His His Asn Leu Ser Trp Glu Cys
1               5

<210> SEQ ID NO 8
<211> LENGTH: 9
<212> TYPE: PRT
<213> ORGANISM: Artificial sequence
<220> FEATURE:
<223> OTHER INFORMATION: Synthetic peptide

<400> SEQUENCE: 8

Cys His Ile Trp Thr Leu Ala Ser Cys
1               5

<210> SEQ ID NO 9
<211> LENGTH: 9
<212> TYPE: PRT
```

```
<213> ORGANISM: Artificial sequence
<220> FEATURE:
<223> OTHER INFORMATION: Synthetic peptide

<400> SEQUENCE: 9

Cys His Asn Thr Phe Ser Pro Arg Cys
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic peptide

<400> SEQUENCE: 10

Cys Ile Pro Leu His Ala Ser Leu Cys
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic peptide

<400> SEQUENCE: 11

Cys Ile Thr Thr Thr Ser Leu Ser Cys
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic peptide

<400> SEQUENCE: 12

Cys Lys Leu Thr Thr Cys Lys Asp Cys
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic peptide

<400> SEQUENCE: 13

Cys Lys Asn His Thr Thr Phe Trp Cys
1               5

<210> SEQ ID NO 14
<211> LENGTH: 9
<212> TYPE: PRT
<213> ORGANISM: Artificial sequence
<220> FEATURE:
<223> OTHER INFORMATION: Synthetic peptide

<400> SEQUENCE: 14

Cys Leu Lys Leu Leu Ser Arg Ser Cys
1               5

<210> SEQ ID NO 15
<211> LENGTH: 9
<212> TYPE: PRT
<213> ORGANISM: Artificial sequence
```

```
<220> FEATURE:
<223> OTHER INFORMATION: Synthetic peptide

<400> SEQUENCE: 15

Cys Leu Leu Lys Ala His Pro Ser Cys
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic peptide

<400> SEQUENCE: 16

Cys Leu Asn Gln Leu Lys Gln Ala Cys
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic peptide

<400> SEQUENCE: 17

Cys Met Asn Phe Pro Ser Pro His Cys
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic peptide

<400> SEQUENCE: 18

Cys Pro Gln Ser Pro Thr Tyr Thr Cys
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic peptide

<400> SEQUENCE: 19

Cys Pro Ser Ser Ala Ile His Thr Cys
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic peptide

<400> SEQUENCE: 20

Cys Pro Thr Ser Thr Ala Arg Ile Cys
1               5

<210> SEQ ID NO 21
<211> LENGTH: 9
<212> TYPE: PRT
<213> ORGANISM: Artificial sequence
<220> FEATURE:
```

<223> OTHER INFORMATION: Synthetic peptide

<400> SEQUENCE: 21

Cys Gln Ala Ser Ser Phe Pro Ser Cys
1               5

<210> SEQ ID NO 22
<211> LENGTH: 9
<212> TYPE: PRT
<213> ORGANISM: Artificial sequence
<220> FEATURE:
<223> OTHER INFORMATION: Synthetic peptide

<400> SEQUENCE: 22

Cys Gln Pro Tyr Phe Trp Tyr Arg Cys
1               5

<210> SEQ ID NO 23
<211> LENGTH: 9
<212> TYPE: PRT
<213> ORGANISM: Artificial sequence
<220> FEATURE:
<223> OTHER INFORMATION: Synthetic peptide

<400> SEQUENCE: 23

Cys Gln Thr Leu Thr Pro Ser Ile Cys
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic peptide

<400> SEQUENCE: 24

Cys Ser Lys Leu Gly His Leu Trp Cys
1               5

<210> SEQ ID NO 25
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Any amino acid

<400> SEQUENCE: 25

Cys Ser Lys Thr Pro Glu Arg Ile Xaa
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic peptide

<400> SEQUENCE: 26

Cys Ser Asn Asn Asn Arg Met Thr Cys
1               5

<210> SEQ ID NO 27
<211> LENGTH: 9

```
<212> TYPE: PRT
<213> ORGANISM: Artificial sequence
<220> FEATURE:
<223> OTHER INFORMATION: Synthetic peptide

<400> SEQUENCE: 27

Cys Ser Pro Ile Leu Ser Leu Ser Cys
1               5

<210> SEQ ID NO 28
<211> LENGTH: 9
<212> TYPE: PRT
<213> ORGANISM: Artificial sequence
<220> FEATURE:
<223> OTHER INFORMATION: Synthetic peptide

<400> SEQUENCE: 28

Cys Ser Pro Thr Asn Phe Thr Arg Cys
1               5

<210> SEQ ID NO 29
<211> LENGTH: 9
<212> TYPE: PRT
<213> ORGANISM: Artificial sequence
<220> FEATURE:
<223> OTHER INFORMATION: Synthetic peptide

<400> SEQUENCE: 29

Cys Ser Arg Pro Ala Met Asn Val Cys
1               5

<210> SEQ ID NO 30
<211> LENGTH: 9
<212> TYPE: PRT
<213> ORGANISM: Artificial sequence
<220> FEATURE:
<223> OTHER INFORMATION: Synthetic peptide

<400> SEQUENCE: 30

Cys Ser Thr Lys Ala Tyr Pro Asn Cys
1               5

<210> SEQ ID NO 31
<211> LENGTH: 9
<212> TYPE: PRT
<213> ORGANISM: Artificial sequence
<220> FEATURE:
<223> OTHER INFORMATION: Synthetic peptide

<400> SEQUENCE: 31

Cys Ser Thr Ser Ser Cys Gly Ser Cys
1               5

<210> SEQ ID NO 32
<211> LENGTH: 9
<212> TYPE: PRT
<213> ORGANISM: Artificial sequence
<220> FEATURE:
<223> OTHER INFORMATION: Synthetic peptide

<400> SEQUENCE: 32

Cys Ser Tyr Trp Gly His Arg Asp Cys
1               5

<210> SEQ ID NO 33
<211> LENGTH: 9
<212> TYPE: PRT
```

```
<213> ORGANISM: Artificial sequence
<220> FEATURE:
<223> OTHER INFORMATION: Synthetic peptide

<400> SEQUENCE: 33

Cys Thr Ala His Asp Ala Asn Ala Cys
1               5

<210> SEQ ID NO 34
<211> LENGTH: 9
<212> TYPE: PRT
<213> ORGANISM: Artificial sequence
<220> FEATURE:
<223> OTHER INFORMATION: Synthetic peptide

<400> SEQUENCE: 34

Cys Thr Ala Asn Ser Glu Lys Thr Cys
1               5

<210> SEQ ID NO 35
<211> LENGTH: 9
<212> TYPE: PRT
<213> ORGANISM: Artificial sequence
<220> FEATURE:
<223> OTHER INFORMATION: Synthetic peptide

<400> SEQUENCE: 35

Cys Thr His Pro Lys Ala Ser Met Cys
1               5

<210> SEQ ID NO 36
<211> LENGTH: 9
<212> TYPE: PRT
<213> ORGANISM: Artificial sequence
<220> FEATURE:
<223> OTHER INFORMATION: Synthetic peptide

<400> SEQUENCE: 36

Cys Thr Lys Thr Ile Asn Gly Lys Cys
1               5

<210> SEQ ID NO 37
<211> LENGTH: 9
<212> TYPE: PRT
<213> ORGANISM: Artificial sequence
<220> FEATURE:
<223> OTHER INFORMATION: Synthetic peptide

<400> SEQUENCE: 37

Cys Thr Asn Met Gln Ser Pro Leu Cys
1               5

<210> SEQ ID NO 38
<211> LENGTH: 9
<212> TYPE: PRT
<213> ORGANISM: Artificial sequence
<220> FEATURE:
<223> OTHER INFORMATION: Synthetic peptide

<400> SEQUENCE: 38

Cys Thr Pro Phe Thr Lys Leu Pro Cys
1               5

<210> SEQ ID NO 39
<211> LENGTH: 9
<212> TYPE: PRT
<213> ORGANISM: Artificial sequence
```

```
<220> FEATURE:
<223> OTHER INFORMATION: Synthetic peptide

<400> SEQUENCE: 39

Cys Thr Pro Thr Thr Asp Ser Ile Cys
1               5

<210> SEQ ID NO 40
<211> LENGTH: 9
<212> TYPE: PRT
<213> ORGANISM: Artificial sequence
<220> FEATURE:
<223> OTHER INFORMATION: Synthetic peptide

<400> SEQUENCE: 40

Cys Thr Gln Gln Asn Gly His Pro Cys
1               5

<210> SEQ ID NO 41
<211> LENGTH: 10
<212> TYPE: PRT
<213> ORGANISM: Artificial sequence
<220> FEATURE:
<223> OTHER INFORMATION: Synthetic peptide

<400> SEQUENCE: 41

Ala Cys Thr Thr Pro Ser Lys His Gln Cys
1               5                   10

<210> SEQ ID NO 42
<211> LENGTH: 9
<212> TYPE: PRT
<213> ORGANISM: Artificial sequence
<220> FEATURE:
<223> OTHER INFORMATION: Synthetic peptide

<400> SEQUENCE: 42

Cys Thr Tyr Asn Val Ala Lys Pro Cys
1               5

<210> SEQ ID NO 43
<211> LENGTH: 10
<212> TYPE: PRT
<213> ORGANISM: Artificial sequence
<220> FEATURE:
<223> OTHER INFORMATION: Synthetic peptide

<400> SEQUENCE: 43

Ala Cys Ala Pro Leu Met Phe Ser Gln Cys
1               5                   10

<210> SEQ ID NO 44
<211> LENGTH: 10
<212> TYPE: PRT
<213> ORGANISM: Artificial sequence
<220> FEATURE:
<223> OTHER INFORMATION: Synthetic peptide

<400> SEQUENCE: 44

Ala Cys His Ala Ser Leu Lys His Arg Cys
1               5                   10

<210> SEQ ID NO 45
<211> LENGTH: 11
<212> TYPE: PRT
<213> ORGANISM: Artificial sequence
<220> FEATURE:
```

```
<223> OTHER INFORMATION: Synthetic peptide

<400> SEQUENCE: 45

Ala His Phe Ser Pro Asn Leu Leu Leu Gly Gly
1               5                   10

<210> SEQ ID NO 46
<211> LENGTH: 12
<212> TYPE: PRT
<213> ORGANISM: Artificial sequence
<220> FEATURE:
<223> OTHER INFORMATION: Synthetic peptide

<400> SEQUENCE: 46

Ala His Ser Leu Lys Ser Ile Thr Asn His Gly Leu
1               5                   10

<210> SEQ ID NO 47
<211> LENGTH: 12
<212> TYPE: PRT
<213> ORGANISM: Artificial sequence
<220> FEATURE:
<223> OTHER INFORMATION: Synthetic peptide

<400> SEQUENCE: 47

Ala Lys Thr Leu Met Pro Ser Pro Phe Pro Arg Thr
1               5                   10

<210> SEQ ID NO 48
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (12)..(12)
<223> OTHER INFORMATION: Gln, Leu or Gly

<400> SEQUENCE: 48

Ala Ser Ala Val Gly Ser Leu Ser Ile Arg Trp Xaa
1               5                   10

<210> SEQ ID NO 49
<211> LENGTH: 12
<212> TYPE: PRT
<213> ORGANISM: Artificial sequence
<220> FEATURE:
<223> OTHER INFORMATION: Synthetic peptide

<400> SEQUENCE: 49

Ala Ser Trp Val Asp Ser Arg Gln Pro Ser Ala Ala
1               5                   10

<210> SEQ ID NO 50
<211> LENGTH: 11
<212> TYPE: PRT
<213> ORGANISM: Artificial sequence
<220> FEATURE:
<223> OTHER INFORMATION: Synthetic peptide

<400> SEQUENCE: 50

Cys Pro Gln Leu Thr Val Gly Gln His Arg Thr
1               5                   10

<210> SEQ ID NO 51
<211> LENGTH: 12
```

```
<212> TYPE: PRT
<213> ORGANISM: Artificial sequence
<220> FEATURE:
<223> OTHER INFORMATION: Synthetic peptide

<400> SEQUENCE: 51

Asp Leu Pro Pro Thr Leu His Thr Thr Gly Ser Pro
1               5                   10

<210> SEQ ID NO 52
<211> LENGTH: 12
<212> TYPE: PRT
<213> ORGANISM: Artificial sequence
<220> FEATURE:
<223> OTHER INFORMATION: Synthetic peptide

<400> SEQUENCE: 52

Asp Ser Ser Asn Pro Ile Phe Trp Arg Pro Ser Ser
1               5                   10

<210> SEQ ID NO 53
<211> LENGTH: 12
<212> TYPE: PRT
<213> ORGANISM: Artificial sequence
<220> FEATURE:
<223> OTHER INFORMATION: Synthetic peptide

<400> SEQUENCE: 53

Glu Phe Leu Gly Val Pro Ala Ser Leu Val Asn Pro
1               5                   10

<210> SEQ ID NO 54
<211> LENGTH: 12
<212> TYPE: PRT
<213> ORGANISM: Artificial sequence
<220> FEATURE:
<223> OTHER INFORMATION: Synthetic peptide

<400> SEQUENCE: 54

Glu Ser Asp Leu Thr His Ala Leu His Trp Leu Gly
1               5                   10

<210> SEQ ID NO 55
<211> LENGTH: 12
<212> TYPE: PRT
<213> ORGANISM: Artificial sequence
<220> FEATURE:
<223> OTHER INFORMATION: Synthetic peptide

<400> SEQUENCE: 55

Glu Val His Ser Thr Asp Arg Tyr Arg Ser Ile Pro
1               5                   10

<210> SEQ ID NO 56
<211> LENGTH: 12
<212> TYPE: PRT
<213> ORGANISM: Artificial sequence
<220> FEATURE:
<223> OTHER INFORMATION: Synthetic peptide

<400> SEQUENCE: 56

Phe Gly Leu Gln Pro Thr Gly Asp Ile Ala Arg Arg
1               5                   10

<210> SEQ ID NO 57
<211> LENGTH: 12
<212> TYPE: PRT
```

```
<213> ORGANISM: Artificial sequence
<220> FEATURE:
<223> OTHER INFORMATION: Synthetic peptide

<400> SEQUENCE: 57

Phe Ser Met Asp Asp Pro Glu Arg Val Arg Ser Pro
1               5                   10

<210> SEQ ID NO 58
<211> LENGTH: 12
<212> TYPE: PRT
<213> ORGANISM: Artificial sequence
<220> FEATURE:
<223> OTHER INFORMATION: Synthetic peptide

<400> SEQUENCE: 58

Phe Ser Pro Leu His Thr Ser Thr Tyr Arg Pro Ser
1               5                   10

<210> SEQ ID NO 59
<211> LENGTH: 12
<212> TYPE: PRT
<213> ORGANISM: Artificial sequence
<220> FEATURE:
<223> OTHER INFORMATION: Synthetic peptide

<400> SEQUENCE: 59

Gly Asp Phe Asn Ser Gly His His Thr Thr Thr Arg
1               5                   10

<210> SEQ ID NO 60
<211> LENGTH: 12
<212> TYPE: PRT
<213> ORGANISM: Artificial sequence
<220> FEATURE:
<223> OTHER INFORMATION: Synthetic peptide

<400> SEQUENCE: 60

Gly Pro Ser Asn Asn Leu Pro Trp Ser Asn Thr Pro
1               5                   10

<210> SEQ ID NO 61
<211> LENGTH: 12
<212> TYPE: PRT
<213> ORGANISM: Artificial sequence
<220> FEATURE:
<223> OTHER INFORMATION: Synthetic peptide

<400> SEQUENCE: 61

Gly Val His Lys His Phe Tyr Ser Arg Trp Leu Gly
1               5                   10

<210> SEQ ID NO 62
<211> LENGTH: 12
<212> TYPE: PRT
<213> ORGANISM: Artificial sequence
<220> FEATURE:
<223> OTHER INFORMATION: Synthetic peptide

<400> SEQUENCE: 62

His Ala Pro Leu Thr Arg Ser Pro Ala Pro Asn Leu
1               5                   10

<210> SEQ ID NO 63
<211> LENGTH: 12
<212> TYPE: PRT
<213> ORGANISM: Artificial sequence
```

```
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Phe or Leu

<400> SEQUENCE: 63

His Gly Ser Leu Thr Thr Leu Xaa Arg Tyr Glu Pro
1               5                   10

<210> SEQ ID NO 64
<211> LENGTH: 12
<212> TYPE: PRT
<213> ORGANISM: Artificial sequence
<220> FEATURE:
<223> OTHER INFORMATION: Synthetic peptide

<400> SEQUENCE: 64

His His Phe His Leu Pro Lys Leu Arg Pro Pro Val
1               5                   10

<210> SEQ ID NO 65
<211> LENGTH: 12
<212> TYPE: PRT
<213> ORGANISM: Artificial sequence
<220> FEATURE:
<223> OTHER INFORMATION: Synthetic peptide

<400> SEQUENCE: 65

His His Thr Trp Asp Thr Arg Ile Trp Gln Ala Phe
1               5                   10

<210> SEQ ID NO 66
<211> LENGTH: 11
<212> TYPE: PRT
<213> ORGANISM: Artificial sequence
<220> FEATURE:
<223> OTHER INFORMATION: Synthetic peptide

<400> SEQUENCE: 66

His Pro Thr Thr Pro Ile His Met Pro Asn Phe
1               5                   10

<210> SEQ ID NO 67
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Any amino acid
<220> FEATURE:
<221> NAME/KEY: misc_feature
<222> LOCATION: (7)..(7)
<223> OTHER INFORMATION: Pro or no amino acid
<220> FEATURE:
<221> NAME/KEY: misc_feature
<222> LOCATION: (11)..(11)
<223> OTHER INFORMATION: Ala or Gly

<400> SEQUENCE: 67

His Arg Asp Pro Xaa Ser Xaa Pro Ser Ala Xaa Arg Pro
1               5                   10

<210> SEQ ID NO 68
<211> LENGTH: 12
```

```
<212> TYPE: PRT
<213> ORGANISM: Artificial sequence
<220> FEATURE:
<223> OTHER INFORMATION: Synthetic peptide

<400> SEQUENCE: 68

His Asn Val Thr Thr Arg Thr Gln Arg Leu Met Pro
1               5                   10

<210> SEQ ID NO 69
<211> LENGTH: 12
<212> TYPE: PRT
<213> ORGANISM: Artificial sequence
<220> FEATURE:
<223> OTHER INFORMATION: Synthetic peptide

<400> SEQUENCE: 69

His Ser Ala Cys His Ala Ser Leu Lys His Arg Cys
1               5                   10

<210> SEQ ID NO 70
<211> LENGTH: 12
<212> TYPE: PRT
<213> ORGANISM: Artificial sequence
<220> FEATURE:
<223> OTHER INFORMATION: Synthetic peptide

<400> SEQUENCE: 70

His Ser Ala Cys Lys Leu Thr Thr Cys Lys Asp Gly
1               5                   10

<210> SEQ ID NO 71
<211> LENGTH: 12
<212> TYPE: PRT
<213> ORGANISM: Artificial sequence
<220> FEATURE:
<223> OTHER INFORMATION: Synthetic peptide

<400> SEQUENCE: 71

His Ser Ala Cys Leu Ser Thr Lys Thr Asn Ile Cys
1               5                   10

<210> SEQ ID NO 72
<211> LENGTH: 12
<212> TYPE: PRT
<213> ORGANISM: Artificial sequence
<220> FEATURE:
<223> OTHER INFORMATION: Synthetic peptide

<400> SEQUENCE: 72

Ile Ala His Val Pro Glu Thr Arg Leu Ala Gln Met
1               5                   10

<210> SEQ ID NO 73
<211> LENGTH: 12
<212> TYPE: PRT
<213> ORGANISM: Artificial sequence
<220> FEATURE:
<223> OTHER INFORMATION: Synthetic peptide

<400> SEQUENCE: 73

Ile Phe Ser Met Gly Thr Ala Leu Ala Arg Pro Leu
1               5                   10

<210> SEQ ID NO 74
<211> LENGTH: 12
<212> TYPE: PRT
```

<213> ORGANISM: Artificial sequence
<220> FEATURE:
<223> OTHER INFORMATION: Synthetic peptide

<400> SEQUENCE: 74

Ile Asn Lys His Pro Gln Gln Val Ser Thr Leu Leu
1               5                   10

<210> SEQ ID NO 75
<211> LENGTH: 12
<212> TYPE: PRT
<213> ORGANISM: Artificial sequence
<220> FEATURE:
<223> OTHER INFORMATION: Synthetic peptide

<400> SEQUENCE: 75

Ile Ser Pro Ser His Ser Gln Ala Gln Ala Asp Leu
1               5                   10

<210> SEQ ID NO 76
<211> LENGTH: 12
<212> TYPE: PRT
<213> ORGANISM: Artificial sequence
<220> FEATURE:
<223> OTHER INFORMATION: Synthetic peptide

<400> SEQUENCE: 76

Leu Asp Tyr Pro Ile Pro Gln Thr Val Leu His His
1               5                   10

<210> SEQ ID NO 77
<211> LENGTH: 12
<212> TYPE: PRT
<213> ORGANISM: Artificial sequence
<220> FEATURE:
<223> OTHER INFORMATION: Synthetic peptide

<400> SEQUENCE: 77

Leu Phe Ala Ala Val Pro Ser Thr Gln Phe Phe Arg
1               5                   10

<210> SEQ ID NO 78
<211> LENGTH: 12
<212> TYPE: PRT
<213> ORGANISM: Artificial sequence
<220> FEATURE:
<223> OTHER INFORMATION: Synthetic peptide

<400> SEQUENCE: 78

Leu Gly Phe Asp Pro Thr Ser Thr Arg Phe Tyr Thr
1               5                   10

<210> SEQ ID NO 79
<211> LENGTH: 12
<212> TYPE: PRT
<213> ORGANISM: Artificial sequence
<220> FEATURE:
<223> OTHER INFORMATION: Synthetic peptide

<400> SEQUENCE: 79

Leu Leu Ala Asp Thr Thr His His Arg Pro Trp Pro
1               5                   10

<210> SEQ ID NO 80
<211> LENGTH: 12
<212> TYPE: PRT
<213> ORGANISM: Artificial sequence

```
<220> FEATURE:
<223> OTHER INFORMATION: Synthetic peptide

<400> SEQUENCE: 80

Leu Pro Trp Ala Pro Asn Leu Pro Asp Ser Thr Ala
1               5                   10

<210> SEQ ID NO 81
<211> LENGTH: 12
<212> TYPE: PRT
<213> ORGANISM: Artificial sequence
<220> FEATURE:
<223> OTHER INFORMATION: Synthetic peptide

<400> SEQUENCE: 81

Leu Gln Pro Ser Gln Pro Gln Arg Phe Ala Pro Thr
1               5                   10

<210> SEQ ID NO 82
<211> LENGTH: 12
<212> TYPE: PRT
<213> ORGANISM: Artificial sequence
<220> FEATURE:
<223> OTHER INFORMATION: Synthetic peptide

<400> SEQUENCE: 82

Leu Ser Pro Pro Met Gln Leu Gln Pro Thr Tyr Ser
1               5                   10

<210> SEQ ID NO 83
<211> LENGTH: 12
<212> TYPE: PRT
<213> ORGANISM: Artificial sequence
<220> FEATURE:
<223> OTHER INFORMATION: Synthetic peptide

<400> SEQUENCE: 83

Met His Asn Val Ser Asp Ser Asn Asp Ser Ala Ile
1               5                   10

<210> SEQ ID NO 84
<211> LENGTH: 12
<212> TYPE: PRT
<213> ORGANISM: Artificial sequence
<220> FEATURE:
<223> OTHER INFORMATION: Synthetic peptide

<400> SEQUENCE: 84

Asn Ser Ser Met Leu Gly Met Leu Pro Ser Ser Phe
1               5                   10

<210> SEQ ID NO 85
<211> LENGTH: 12
<212> TYPE: PRT
<213> ORGANISM: Artificial sequence
<220> FEATURE:
<223> OTHER INFORMATION: Synthetic peptide

<400> SEQUENCE: 85

Asn Thr Ser Ser Ser Gln Gly Thr Gln Arg Leu Gly
1               5                   10

<210> SEQ ID NO 86
<211> LENGTH: 12
<212> TYPE: PRT
<213> ORGANISM: Artificial sequence
<220> FEATURE:
```

```
<223> OTHER INFORMATION: Synthetic peptide

<400> SEQUENCE: 86

Pro Gly Gln Trp Pro Ser Ser Leu Thr Leu Tyr Lys
1               5                   10

<210> SEQ ID NO 87
<211> LENGTH: 12
<212> TYPE: PRT
<213> ORGANISM: Artificial sequence
<220> FEATURE:
<223> OTHER INFORMATION: Synthetic peptide

<400> SEQUENCE: 87

Gln Ile Pro Gln Met Arg Ile Leu His Pro Tyr Gly
1               5                   10

<210> SEQ ID NO 88
<211> LENGTH: 12
<212> TYPE: PRT
<213> ORGANISM: Artificial sequence
<220> FEATURE:
<223> OTHER INFORMATION: Synthetic peptide

<400> SEQUENCE: 88

Gln Ile Gln Lys Pro Pro Arg Thr Pro Pro Ser Leu
1               5                   10

<210> SEQ ID NO 89
<211> LENGTH: 12
<212> TYPE: PRT
<213> ORGANISM: Artificial sequence
<220> FEATURE:
<223> OTHER INFORMATION: Synthetic peptide

<400> SEQUENCE: 89

Gln Leu Thr Gln Thr Met Trp Lys Asp Thr Thr Leu
1               5                   10

<210> SEQ ID NO 90
<211> LENGTH: 12
<212> TYPE: PRT
<213> ORGANISM: Artificial sequence
<220> FEATURE:
<223> OTHER INFORMATION: Synthetic peptide

<400> SEQUENCE: 90

Gln Asn Leu Pro Pro Glu Arg Tyr Ser Glu Ala Thr
1               5                   10

<210> SEQ ID NO 91
<211> LENGTH: 12
<212> TYPE: PRT
<213> ORGANISM: Artificial sequence
<220> FEATURE:
<223> OTHER INFORMATION: Synthetic peptide

<400> SEQUENCE: 91

Gln Ser Leu Ser Phe Ala Gly Pro Pro Ala Trp Gln
1               5                   10

<210> SEQ ID NO 92
<211> LENGTH: 12
<212> TYPE: PRT
<213> ORGANISM: Artificial sequence
<220> FEATURE:
<223> OTHER INFORMATION: Synthetic peptide
```

-continued

<400> SEQUENCE: 92

Gln Thr Thr Met Thr Pro Leu Trp Pro Ser Phe Ser
1               5                   10

<210> SEQ ID NO 93
<211> LENGTH: 12
<212> TYPE: PRT
<213> ORGANISM: Artificial sequence
<220> FEATURE:
<223> OTHER INFORMATION: Synthetic peptide

<400> SEQUENCE: 93

Arg Cys Met Ser Glu Val Ile Ser Phe Asn Cys Pro
1               5                   10

<210> SEQ ID NO 94
<211> LENGTH: 12
<212> TYPE: PRT
<213> ORGANISM: Artificial sequence
<220> FEATURE:
<223> OTHER INFORMATION: Synthetic peptide

<400> SEQUENCE: 94

Arg Ser Pro Tyr Tyr Asn Lys Trp Ser Ser Lys Phe
1               5                   10

<210> SEQ ID NO 95
<211> LENGTH: 12
<212> TYPE: PRT
<213> ORGANISM: Artificial sequence
<220> FEATURE:
<223> OTHER INFORMATION: Synthetic peptide

<400> SEQUENCE: 95

Ser Ala Gly His Ile His Glu Ala His Arg Pro Leu
1               5                   10

<210> SEQ ID NO 96
<211> LENGTH: 12
<212> TYPE: PRT
<213> ORGANISM: Artificial sequence
<220> FEATURE:
<223> OTHER INFORMATION: Synthetic peptide

<400> SEQUENCE: 96

Ser Ala Ile Ser Asp His Arg Ala His Arg Ser His
1               5                   10

<210> SEQ ID NO 97
<211> LENGTH: 12
<212> TYPE: PRT
<213> ORGANISM: Artificial sequence
<220> FEATURE:
<223> OTHER INFORMATION: Synthetic peptide

<400> SEQUENCE: 97

Ser Glu Pro Thr Tyr Trp Arg Pro Asn Met Ser Gly
1               5                   10

<210> SEQ ID NO 98
<211> LENGTH: 12
<212> TYPE: PRT
<213> ORGANISM: Artificial sequence
<220> FEATURE:
<223> OTHER INFORMATION: Synthetic peptide

```
<400> SEQUENCE: 98

Ser Phe Ala Pro Asp Ile Lys Tyr Pro Val Pro Ser
1               5                   10

<210> SEQ ID NO 99
<211> LENGTH: 12
<212> TYPE: PRT
<213> ORGANISM: Artificial sequence
<220> FEATURE:
<223> OTHER INFORMATION: Synthetic peptide

<400> SEQUENCE: 99

Ser Phe Trp His His His Ser Pro Arg Ser Pro Leu
1               5                   10

<210> SEQ ID NO 100
<211> LENGTH: 12
<212> TYPE: PRT
<213> ORGANISM: Artificial sequence
<220> FEATURE:
<223> OTHER INFORMATION: Synthetic peptide

<400> SEQUENCE: 100

Ser Ile Phe Ala His Gln Thr Pro Thr His Lys Asn
1               5                   10

<210> SEQ ID NO 101
<211> LENGTH: 12
<212> TYPE: PRT
<213> ORGANISM: Artificial sequence
<220> FEATURE:
<223> OTHER INFORMATION: Synthetic peptide

<400> SEQUENCE: 101

Ser Ile Pro Ser His Ser Ile His Ser Ala Lys Ala
1               5                   10

<210> SEQ ID NO 102
<211> LENGTH: 12
<212> TYPE: PRT
<213> ORGANISM: Artificial sequence
<220> FEATURE:
<223> OTHER INFORMATION: Synthetic peptide

<400> SEQUENCE: 102

Ser Ile Arg Thr Ser Met Asn Pro Pro Asn Leu Leu
1               5                   10

<210> SEQ ID NO 103
<211> LENGTH: 12
<212> TYPE: PRT
<213> ORGANISM: Artificial sequence
<220> FEATURE:
<223> OTHER INFORMATION: Synthetic peptide

<400> SEQUENCE: 103

Ser Leu Pro His Tyr Ile Asp Asn Pro Phe Arg Gln
1               5                   10

<210> SEQ ID NO 104
<211> LENGTH: 12
<212> TYPE: PRT
<213> ORGANISM: Artificial sequence
<220> FEATURE:
<223> OTHER INFORMATION: Synthetic peptide

<400> SEQUENCE: 104
```

Ser Leu Ser Lys Ala Asn Ile Leu His Leu Tyr Gly
1               5                   10

<210> SEQ ID NO 105
<211> LENGTH: 12
<212> TYPE: PRT
<213> ORGANISM: Artificial sequence
<220> FEATURE:
<223> OTHER INFORMATION: Synthetic peptide

<400> SEQUENCE: 105

Ser Leu Val Thr Ala Asp Ala Ser Phe Thr Pro Ser
1               5                   10

<210> SEQ ID NO 106
<211> LENGTH: 12
<212> TYPE: PRT
<213> ORGANISM: Artificial sequence
<220> FEATURE:
<223> OTHER INFORMATION: Synthetic peptide

<400> SEQUENCE: 106

Ser Met Val Tyr Gly Asn Arg Leu Pro Ser Ala Leu
1               5                   10

<210> SEQ ID NO 107
<211> LENGTH: 12
<212> TYPE: PRT
<213> ORGANISM: Artificial sequence
<220> FEATURE:
<223> OTHER INFORMATION: Synthetic peptide

<400> SEQUENCE: 107

Ser Pro Ser Leu Met Ala Arg Ser Ser Pro Tyr Trp
1               5                   10

<210> SEQ ID NO 108
<211> LENGTH: 12
<212> TYPE: PRT
<213> ORGANISM: Artificial sequence
<220> FEATURE:
<223> OTHER INFORMATION: Synthetic peptide

<400> SEQUENCE: 108

Ser Pro Asn Leu Pro Trp Ser Lys Leu Ser Ala Tyr
1               5                   10

<210> SEQ ID NO 109
<211> LENGTH: 12
<212> TYPE: PRT
<213> ORGANISM: Artificial sequence
<220> FEATURE:
<223> OTHER INFORMATION: Synthetic peptide

<400> SEQUENCE: 109

Ser Gln Thr Leu Pro Tyr Ser Asn Ala Pro Ser Pro
1               5                   10

<210> SEQ ID NO 110
<211> LENGTH: 12
<212> TYPE: PRT
<213> ORGANISM: Artificial sequence
<220> FEATURE:
<223> OTHER INFORMATION: Synthetic peptide

<400> SEQUENCE: 110

Ser Ser Thr Gln Ala His Pro Phe Ala Pro Gln Leu
1               5                   10

<210> SEQ ID NO 111
<211> LENGTH: 12
<212> TYPE: PRT
<213> ORGANISM: Artificial sequence
<220> FEATURE:
<223> OTHER INFORMATION: Synthetic peptide

<400> SEQUENCE: 111

Ser Thr Pro Asn Ser Tyr Ser Leu Pro Gln Ala Arg
1               5                   10

<210> SEQ ID NO 112
<211> LENGTH: 12
<212> TYPE: PRT
<213> ORGANISM: Artificial sequence
<220> FEATURE:
<223> OTHER INFORMATION: Synthetic peptide

<400> SEQUENCE: 112

Ser Thr Val Val Met Gln Pro Pro Arg Pro Ala
1               5                   10

<210> SEQ ID NO 113
<211> LENGTH: 12
<212> TYPE: PRT
<213> ORGANISM: Artificial sequence
<220> FEATURE:
<223> OTHER INFORMATION: Synthetic peptide

<400> SEQUENCE: 113

Ser Val Gln Thr Arg Pro Leu Phe His Ser His Phe
1               5                   10

<210> SEQ ID NO 114
<211> LENGTH: 12
<212> TYPE: PRT
<213> ORGANISM: Artificial sequence
<220> FEATURE:
<223> OTHER INFORMATION: Synthetic peptide

<400> SEQUENCE: 114

Ser Val Ser Val Gly Met Lys Pro Ser Pro Arg Pro
1               5                   10

<210> SEQ ID NO 115
<211> LENGTH: 12
<212> TYPE: PRT
<213> ORGANISM: Artificial sequence
<220> FEATURE:
<223> OTHER INFORMATION: Synthetic peptide

<400> SEQUENCE: 115

Ser Tyr Ile Asp Ser Met Val Pro Ser Thr Gln Thr
1               5                   10

<210> SEQ ID NO 116
<211> LENGTH: 12
<212> TYPE: PRT
<213> ORGANISM: Artificial sequence
<220> FEATURE:
<223> OTHER INFORMATION: Synthetic peptide

<400> SEQUENCE: 116

Ser Tyr Lys Thr Thr Asp Ser Asp Thr Ser Pro Leu

```
                1               5                   10
```

<210> SEQ ID NO 117
<211> LENGTH: 12
<212> TYPE: PRT
<213> ORGANISM: Artificial sequence
<220> FEATURE:
<223> OTHER INFORMATION: Synthetic peptide

<400> SEQUENCE: 117

```
Thr Ala Ala Ala Ser Asn Leu Arg Ala Val Pro Pro
1               5                   10
```

<210> SEQ ID NO 118
<211> LENGTH: 12
<212> TYPE: PRT
<213> ORGANISM: Artificial sequence
<220> FEATURE:
<223> OTHER INFORMATION: Synthetic peptide

<400> SEQUENCE: 118

```
Thr Ala Pro Leu Ser His Pro Pro Arg Pro Gly Ala
1               5                   10
```

<210> SEQ ID NO 119
<211> LENGTH: 12
<212> TYPE: PRT
<213> ORGANISM: Artificial sequence
<220> FEATURE:
<223> OTHER INFORMATION: Synthetic peptide

<400> SEQUENCE: 119

```
Thr Gly Leu Leu Pro Asn Ser Ser Gly Ala Gly Ile
1               5                   10
```

<210> SEQ ID NO 120
<211> LENGTH: 12
<212> TYPE: PRT
<213> ORGANISM: Artificial sequence
<220> FEATURE:
<223> OTHER INFORMATION: Synthetic peptide

<400> SEQUENCE: 120

```
Thr Gly Pro Pro Ser Arg Gln Pro Ala Pro Leu His
1               5                   10
```

<210> SEQ ID NO 121
<211> LENGTH: 12
<212> TYPE: PRT
<213> ORGANISM: Artificial sequence
<220> FEATURE:
<223> OTHER INFORMATION: Synthetic peptide

<400> SEQUENCE: 121

```
Thr Leu Ser Asn Gly His Arg Tyr Leu Glu Leu Leu
1               5                   10
```

<210> SEQ ID NO 122
<211> LENGTH: 12
<212> TYPE: PRT
<213> ORGANISM: Artificial sequence
<220> FEATURE:
<223> OTHER INFORMATION: Synthetic peptide

<400> SEQUENCE: 122

```
Thr Pro Ser Pro Lys Leu Leu Gln Val Phe Gln Ala
1               5                   10
```

<210> SEQ ID NO 123
<211> LENGTH: 12
<212> TYPE: PRT
<213> ORGANISM: Artificial sequence
<220> FEATURE:
<223> OTHER INFORMATION: Synthetic peptide

<400> SEQUENCE: 123

Thr Pro Ser Thr Gly Leu Gly Met Ser Pro Ala Val
1               5                   10

<210> SEQ ID NO 124
<211> LENGTH: 12
<212> TYPE: PRT
<213> ORGANISM: Artificial sequence
<220> FEATURE:
<223> OTHER INFORMATION: Synthetic peptide

<400> SEQUENCE: 124

Thr Pro Val Tyr Ser Leu Lys Leu Gly Pro Trp Pro
1               5                   10

<210> SEQ ID NO 125
<211> LENGTH: 12
<212> TYPE: PRT
<213> ORGANISM: Artificial sequence
<220> FEATURE:
<223> OTHER INFORMATION: Synthetic peptide

<400> SEQUENCE: 125

Thr Arg Leu Val Pro Ser Arg Tyr Tyr His His Pro
1               5                   10

<210> SEQ ID NO 126
<211> LENGTH: 12
<212> TYPE: PRT
<213> ORGANISM: Artificial sequence
<220> FEATURE:
<223> OTHER INFORMATION: Synthetic peptide

<400> SEQUENCE: 126

Thr Ser Pro Ile Pro Gln Met Arg Thr Val Pro Pro
1               5                   10

<210> SEQ ID NO 127
<211> LENGTH: 12
<212> TYPE: PRT
<213> ORGANISM: Artificial sequence
<220> FEATURE:
<223> OTHER INFORMATION: Synthetic peptide

<400> SEQUENCE: 127

Thr Thr Asn Ser Ser Met Thr Met Gln Leu Gln Arg
1               5                   10

<210> SEQ ID NO 128
<211> LENGTH: 12
<212> TYPE: PRT
<213> ORGANISM: Artificial sequence
<220> FEATURE:
<223> OTHER INFORMATION: Synthetic peptide

<400> SEQUENCE: 128

Thr Thr Thr Leu Pro Val Gln Pro Thr Leu Arg Asn
1               5                   10

```
<210> SEQ ID NO 129
<211> LENGTH: 12
<212> TYPE: PRT
<213> ORGANISM: Artificial sequence
<220> FEATURE:
<223> OTHER INFORMATION: Synthetic peptide

<400> SEQUENCE: 129

Thr Thr Thr Trp Thr Thr Thr Ala Arg Trp Pro Leu
1               5                   10

<210> SEQ ID NO 130
<211> LENGTH: 12
<212> TYPE: PRT
<213> ORGANISM: Artificial sequence
<220> FEATURE:
<223> OTHER INFORMATION: Synthetic peptide

<400> SEQUENCE: 130

Thr Val Ala Gln Met Pro Pro His Trp Gln Leu Thr
1               5                   10

<210> SEQ ID NO 131
<211> LENGTH: 12
<212> TYPE: PRT
<213> ORGANISM: Artificial sequence
<220> FEATURE:
<223> OTHER INFORMATION: Synthetic peptide

<400> SEQUENCE: 131

Thr Trp Asn Ser Asn Ser Thr Gln Tyr Gly Asn Arg
1               5                   10

<210> SEQ ID NO 132
<211> LENGTH: 12
<212> TYPE: PRT
<213> ORGANISM: Artificial sequence
<220> FEATURE:
<223> OTHER INFORMATION: Synthetic peptide

<400> SEQUENCE: 132

Thr Trp Thr Leu Pro Ala Met His Pro Arg Pro Ala
1               5                   10

<210> SEQ ID NO 133
<211> LENGTH: 12
<212> TYPE: PRT
<213> ORGANISM: Artificial sequence
<220> FEATURE:
<223> OTHER INFORMATION: Synthetic peptide

<400> SEQUENCE: 133

Val His Thr Ser Leu Leu Gln Lys His Pro Leu Pro
1               5                   10

<210> SEQ ID NO 134
<211> LENGTH: 11
<212> TYPE: PRT
<213> ORGANISM: Artificial sequence
<220> FEATURE:
<223> OTHER INFORMATION: Synthetic peptide

<400> SEQUENCE: 134

Val Leu Pro Asn Ile Tyr Met Thr Leu Ser Ala
1               5                   10
```

```
<210> SEQ ID NO 135
<211> LENGTH: 12
<212> TYPE: PRT
<213> ORGANISM: Artificial sequence
<220> FEATURE:
<223> OTHER INFORMATION: Synthetic peptide

<400> SEQUENCE: 135

Val Met Asp Phe Ala Ser Pro Ala His Val Leu Pro
1               5                   10

<210> SEQ ID NO 136
<211> LENGTH: 12
<212> TYPE: PRT
<213> ORGANISM: Artificial sequence
<220> FEATURE:
<223> OTHER INFORMATION: Synthetic peptide

<400> SEQUENCE: 136

Val Asn Gln Glu Tyr Trp Phe Phe Pro Arg Arg Pro
1               5                   10

<210> SEQ ID NO 137
<211> LENGTH: 11
<212> TYPE: PRT
<213> ORGANISM: Artificial sequence
<220> FEATURE:
<223> OTHER INFORMATION: Synthetic peptide

<400> SEQUENCE: 137

Val Tyr Ser Ser Pro Leu Ser Gln Leu Pro Arg
1               5                   10

<210> SEQ ID NO 138
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Arg or no amino acid
<220> FEATURE:
<221> NAME/KEY: misc_feature
<222> LOCATION: (11)..(11)
<223> OTHER INFORMATION: Leu or no amino acid
<220> FEATURE:
<221> NAME/KEY: misc_feature
<222> LOCATION: (14)..(14)
<223> OTHER INFORMATION: Lys or no amino acid

<400> SEQUENCE: 138

Val Pro Pro Ile Ser Xaa Thr Phe Leu Phe Xaa Ser Thr Xaa Ser
1               5                   10                  15

<210> SEQ ID NO 139
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (11)..(11)
<223> OTHER INFORMATION: Any amino acid

<400> SEQUENCE: 139

Val Pro Pro Leu His Pro Ala Leu Ser Arg Xaa Asn
1               5                   10
```

<210> SEQ ID NO 140
<211> LENGTH: 12
<212> TYPE: PRT
<213> ORGANISM: Artificial sequence
<220> FEATURE:
<223> OTHER INFORMATION: Synthetic peptide

<400> SEQUENCE: 140

Val Ser Pro Phe Leu Ser Pro Thr Pro Leu Leu Phe
1               5                   10

<210> SEQ ID NO 141
<211> LENGTH: 12
<212> TYPE: PRT
<213> ORGANISM: Artificial sequence
<220> FEATURE:
<223> OTHER INFORMATION: Synthetic peptide

<400> SEQUENCE: 141

Val Ser Arg Leu Gly Thr Pro Ser Met His Pro Ser
1               5                   10

<210> SEQ ID NO 142
<211> LENGTH: 12
<212> TYPE: PRT
<213> ORGANISM: Artificial sequence
<220> FEATURE:
<223> OTHER INFORMATION: Synthetic peptide

<400> SEQUENCE: 142

Trp Pro Phe Asn His Phe Pro Trp Trp Asn Val Pro
1               5                   10

<210> SEQ ID NO 143
<211> LENGTH: 12
<212> TYPE: PRT
<213> ORGANISM: Artificial sequence
<220> FEATURE:
<223> OTHER INFORMATION: Synthetic peptide

<400> SEQUENCE: 143

Trp Ser Ala His Ile Val Pro Tyr Ser His Lys Pro
1               5                   10

<210> SEQ ID NO 144
<211> LENGTH: 12
<212> TYPE: PRT
<213> ORGANISM: Artificial sequence
<220> FEATURE:
<223> OTHER INFORMATION: Synthetic peptide

<400> SEQUENCE: 144

Trp Trp Pro Asn Ser Leu Asn Trp Val Pro Arg Pro
1               5                   10

<210> SEQ ID NO 145
<211> LENGTH: 12
<212> TYPE: PRT
<213> ORGANISM: Artificial sequence
<220> FEATURE:
<223> OTHER INFORMATION: Synthetic peptide

<400> SEQUENCE: 145

Tyr Ala Thr Gln His Asn Trp Arg Leu Lys His Glu
1               5                   10

```
<210> SEQ ID NO 146
<211> LENGTH: 10
<212> TYPE: PRT
<213> ORGANISM: Artificial sequence
<220> FEATURE:
<223> OTHER INFORMATION: Synthetic peptide

<400> SEQUENCE: 146

Tyr Cys Pro Met Arg Leu Cys Thr Asp Cys
1               5                   10

<210> SEQ ID NO 147
<211> LENGTH: 12
<212> TYPE: PRT
<213> ORGANISM: Artificial sequence
<220> FEATURE:
<223> OTHER INFORMATION: Synthetic peptide

<400> SEQUENCE: 147

Tyr Gly Lys Gly Phe Ser Pro Tyr Phe His Val Thr
1               5                   10

<210> SEQ ID NO 148
<211> LENGTH: 12
<212> TYPE: PRT
<213> ORGANISM: Artificial sequence
<220> FEATURE:
<223> OTHER INFORMATION: Synthetic peptide

<400> SEQUENCE: 148

Tyr Pro His Tyr Ser Leu Pro Gly Ser Ser Thr Leu
1               5                   10

<210> SEQ ID NO 149
<211> LENGTH: 12
<212> TYPE: PRT
<213> ORGANISM: Artificial sequence
<220> FEATURE:
<223> OTHER INFORMATION: Synthetic peptide

<400> SEQUENCE: 149

Tyr Pro Ser Leu Leu Lys Met Gln Pro Gln Phe Ser
1               5                   10

<210> SEQ ID NO 150
<211> LENGTH: 12
<212> TYPE: PRT
<213> ORGANISM: Artificial sequence
<220> FEATURE:
<223> OTHER INFORMATION: Synthetic peptide

<400> SEQUENCE: 150

Tyr Gln Pro Arg Pro Phe Val Thr Thr Ser Pro Met
1               5                   10

<210> SEQ ID NO 151
<211> LENGTH: 12
<212> TYPE: PRT
<213> ORGANISM: Artificial sequence
<220> FEATURE:
<223> OTHER INFORMATION: Synthetic peptide

<400> SEQUENCE: 151

Tyr Ser Ala Pro Leu Ala Arg Ser Asn Val Val Met
1               5                   10
```

```
<210> SEQ ID NO 152
<211> LENGTH: 12
<212> TYPE: PRT
<213> ORGANISM: Artificial sequence
<220> FEATURE:
<223> OTHER INFORMATION: Synthetic peptide

<400> SEQUENCE: 152

Tyr Thr Arg Leu Ser His Asn Pro Tyr Thr Leu Ser
1               5                   10

<210> SEQ ID NO 153
<211> LENGTH: 12
<212> TYPE: PRT
<213> ORGANISM: Artificial sequence
<220> FEATURE:
<223> OTHER INFORMATION: Synthetic peptide

<400> SEQUENCE: 153

Tyr Thr Thr His Val Leu Pro Phe Ala Pro Ser Ser
1               5                   10

<210> SEQ ID NO 154
<211> LENGTH: 12
<212> TYPE: PRT
<213> ORGANISM: Artificial sequence
<220> FEATURE:
<223> OTHER INFORMATION: Synthetic peptide

<400> SEQUENCE: 154

Tyr Thr Trp Gln Thr Ile Arg Glu Gln Tyr Glu Met
1               5                   10

<210> SEQ ID NO 155
<211> LENGTH: 9
<212> TYPE: PRT
<213> ORGANISM: Artificial sequence
<220> FEATURE:
<223> OTHER INFORMATION: Synthetic peptide

<400> SEQUENCE: 155

Cys Leu Ser Thr Lys Thr Asn Ile Cys
1               5

<210> SEQ ID NO 156
<211> LENGTH: 10
<212> TYPE: PRT
<213> ORGANISM: Artificial sequence
<220> FEATURE:
<223> OTHER INFORMATION: Synthetic peptide

<400> SEQUENCE: 156

Ala Cys Leu Ser Thr Lys Thr Asn Ile Cys
1               5                   10

<210> SEQ ID NO 157
<211> LENGTH: 9
<212> TYPE: PRT
<213> ORGANISM: Artificial sequence
<220> FEATURE:
<223> OTHER INFORMATION: Synthetic peptide

<400> SEQUENCE: 157

Cys Thr Thr Pro Ser Lys His Gln Cys
1               5
```